(12) United States Patent
Shyur et al.

(10) Patent No.: US 11,872,260 B2
(45) Date of Patent: Jan. 16, 2024

(54) MINT ESSENTIAL OILS INHIBIT $HRAS^{Q61L}$ MUTANT KERATINOCYTE ACTIVITY AND PREVENT SKIN CARCINOGENESIS

(71) Applicant: ACADEMIA SINICA, Taipei (TW)

(72) Inventors: Lie-Fen Shyur, Taipei (TW);
Chih-Ting Chang, Taichung (TW);
Yuhsin Chen, Taichung (TW)

(73) Assignee: ACADEMIA SINICA, Taipei (TW)

( * ) Notice: Subject to any disclaimer, the term of this patent is extended or adjusted under 35 U.S.C. 154(b) by 2 days.

(21) Appl. No.: 16/585,984

(22) Filed: Sep. 27, 2019

(65) Prior Publication Data
US 2020/0230191 A1  Jul. 23, 2020

Related U.S. Application Data

(60) Provisional application No. 62/739,011, filed on Sep. 28, 2018.

(51) Int. Cl.
*A61K 36/534* (2006.01)
*A61K 31/015* (2006.01)
*A61P 35/00* (2006.01)
*A61K 31/122* (2006.01)
*A61K 9/00* (2006.01)

(52) U.S. Cl.
CPC .......... *A61K 36/534* (2013.01); *A61K 31/015* (2013.01); *A61K 31/122* (2013.01); *A61P 35/00* (2018.01); *A61K 9/0014* (2013.01)

(58) Field of Classification Search
None
See application file for complete search history.

(56) References Cited

PUBLICATIONS

Herman et al., Essential oils and their constituents as skin penetration enhancer for transdermal drug delivery: a review, 2014, J Pharmacy and Pharmacology, 67: 473-485.*

Matsuo et al., a-Pinene isolated from *Schinus terebinthifolius* Raddi (Anacardiaceae) induces apoptosis and confers antimetastatic protection in a melanoma model, 2011, Biochem Biophys Res Comm, 411:449-454.*

Green, Adèle C., and C. M. Olsen. "Cutaneous squamous cell carcinoma: an epidemiological review." British Journal of Dermatology 177.2 (2017): 373-381.

Su, Fei, et al. "RAS mutations in cutaneous squamous-cell carcinomas in patients treated with BRAF inhibitors." New England Journal of Medicine 366.3 (2012): 207-215.

Abel, Erika L., et al. "Multi-stage chemical carcinogenesis in mouse skin: fundamentals and applications." Nature Protocols 4.9 (2009): 1350-1362.

Alexa, Ersilia, et al. "Phytochemical screening and Biological activity of Mentha$^x$ piperita L. and Lavandula angustifolia Mill. extracts." Analytical Cellular Pathology vol. 2018 (2018), 8 pages.

Tsai, Mei-Lin, et al. "Chemical composition and biological properties of essential oils of two mint species." Tropical Journal of Pharmaceutical Research 12.4 (2013): 577-582.

Schutte, B., et al. "Annexin V binding assay as a tool to measure apoptosis in differentiated neuronal cells." Journal of Neuroscience Methods 86.1 (1998): 63-69.

Gracindo, L. A. M. B., et al. "Chemical characterization of mint (*Mentha* spp.) germplasm at Federal District, Brazil." Embrapa Recursos Genéticos e Biotecnologia-Artigo em periódico indexado (ALICE) , vol. 8, p. 5-9 (2006).

Andro, Anca-Raluca; Boz, Irina; Maria-Magdalena Zamfirache, and Ioan Burzo. "Chemical composition of essential oils from Mentha aquatica L. at different moments of the ontogenetic cycle." Journal of Medicinal Plants Research 7.9 (2013): 470-473.

* cited by examiner

*Primary Examiner* — Terry A McKelvey
(74) *Attorney, Agent, or Firm* — DUANE MORRIS LLP

(57) ABSTRACT

This disclosure is directed to essential oils, and methods of their use in treating skin conditions. The skin conditions include those involving $HRAS^{Q61L}$ mutant keratinocyte activity, wherein the essential oil inhibits said activity to treat and/or prevent skin cancer. Particularly, the present invention denotes to and composition for inhibiting and prevent skin carcinogenesis or BRAF inhibitor, a type of anti-cancer drug induced cutaneous side effect.

13 Claims, 14 Drawing Sheets

MINT ESSENTIAL OILS INHIBIT $HRAS^{Q61L}$ MUTANT KERATINOCYTE ACTIVITY AND PREVENT SKIN CARCINOGENESIS

CROSS-REFERENCE TO RELATED APPLICATIONS

This application claims priority to U.S. Provisional Patent Application Ser. No. 62/739,011, filed Sep. 28, 2018, titled "MINT ESSENTIAL OILS INHIBIT HRAS Q61L MUTANT KERATINOCYTE ACTIVITY AND PREVENT SKIN CARCINOGENESIS.

FIELD OF THE INVENTION

The present invention relates to a field of cancer treatment and prevention. Particularly, the present invention denotes to essential oils and composition for inhibiting $HRAS^{Q61L}$ mutant keratinocyte activity and prevent skin carcinogenesis or BRAF inhibitor, a type of anti-cancer drug induced cutaneous side effect.

BACKGROUND OF THE INVENTION

The skin is the largest organ of the human body. It is comprised of two major layers, the epidermis and the dermis. Skin cancer is a frequent type of cancer, particularly in Caucasians. Skin cancers are divided into melanoma and non-melanoma skin cancer (NMSC) including basal cell carcinoma (BCC) and squamous cell carcinoma (SCC). Among skin cancer types, the most malignant is melanoma which is mainly caused by intense UV exposure, especially in those who bear specific genetic mutations.

The main function of melanin is to protect cells from ultraviolet damage. The melanin produced by melanocytes was transferred to keratinocyte and moved to the skin surface to display the skin color. In melanocyte, tyrosinase, an oxidase utilizes tyrosine as the substrate to produce dark brown pigment termed eumelanin or blond red pigment named pheomelanin. The quantity of melanin displays the skin color; however, the excess amount of melanin would cause various skin diseases, including freckles, age spots, and other hyperpigmentation syndrome. NMSC is the most prevalent type of cancer in humans. BCC arises in the skin's basal cells which line the deepest layer of the epidermis. The individual risk factors for BCC include age, gender, ultraviolet exposure, immunosuppression, genetic disease and skin types. SCC originates in keratinocytes in the outermost layer of skin and is more likely to spread to distant areas than BCC. The risk factors for SCC include UV light exposure, immunosuppression, chronic inflammation, arsenic exposure, genetic alteration, smoking, virus infection, and specific drug treatment (A. C. Green and C. M. Olsen., Cutaneous squamous cell carcinoma: An epidemiological review. British Journal Dermatology, 2017. 177(2): p. 373-381).

SUMMARY OF THE INVENTION

In one aspect, the present disclosure provides a method for inhibiting $HRAS^{Q61L}$ mutant keratinocyte activity or treat and/or prevent skin carcinogenesis, comprising topically applying to skin an essential oil composition comprising one or more essential oil from *M. aquatica*, or a composition comprising limonene and carvone and optional one or more essential oil from *M. aquatica*.

In one embodiment, the *M. aquatica* is *M. aquatica* var. Kenting Water Mint or *M. aquatica* var. citrata Lime Mint.

In some embodiments, the essential oil composition is topically applied in an amount ranging from about 0.1 mg to about 10 mg/site. In one embodiment, the essential oil composition is topically applied in an amount of about 5 mg/site. In some embodiments, the essential oil composition is topically applied in an amount ranging from about 0.5 mg to about 10 mg/site, about 1 mg to about 10 mg/site, about 3 mg to about 10 mg/site, about 5 mg to about 10 mg/site, about 7 mg to about 10 mg/site, about 0.1 mg to about 8 mg/site, about 0.1 mg to about 6 mg/site, about 0.1 mg to about 4 mg/site, about 0.1 mg to about 2 mg/site, about 1 mg to about 10 mg/site, about 1 mg to about 8 mg/site, about 1 mg to about 6 mg/site, about 1 mg to about 4 mg/site, about 2 mg to about 10 mg/site, about 2 mg to about 8 mg/site, about 2 mg to about 6 mg/site, about 4 mg to about 10 mg/site, about 4 mg to about 8 mg/site, about 6 mg to about 10 mg/site or about 8 mg to about 10 mg/site.

In some embodiments, the composition comprises about 5% (w/w) to about 70% (w/w) of limonene and about 0.5% (w/w) to about 50% (w/w) of carvone, where the total amount of limonene and carvone does not exceed 100% (w/w). In some embodiments, the amount of limonene ranges from about 5% (w/w) to about 60% (w/w), about 5% (w/w) to about 50% (w/w), about 5% (w/w) to about 40% (w/w), about 5% (w/w) to about 30% (w/w), about 5% (w/w) to about 20% (w/w), about 5% (w/w) to about 10% (w/w), about 10% (w/w) to about 70% (w/w), about 10% (w/w) to about 60% (w/w), about 10% (w/w) to about 50% (w/w), about 10% (w/w) to about 40% (w/w), about 10% (w/w) to about 30% (w/w), about 10% (w/w) to about 20% (w/w), about 20% (w/w) to about 70% (w/w), about 20% (w/w) to about 60% (w/w), about 20% (w/w) to about 50% (w/w), about 20% (w/w) to about 40% (w/w), about 20% (w/w) to about 30% (w/w), about 30% (w/w) to about 70% (w/w), about 30% (w/w) to about 60% (w/w), about 30% (w/w) to about 50% (w/w), about 30% (w/w) to about 40% (w/w), about 40% (w/w) to about 70% (w/w), about 40% (w/w) to about 60% (w/w), about 40% (w/w) to about 50% (w/w), about 50% (w/w) to about 70% (w/w) or about 60% (w/w) to about 70% (w/w). In some embodiments, the amount of carvone ranges from about 0.5% (w/w) to about 40% (w/w) of carvone, about 0.5% (w/w) to about 30% (w/w) of carvone, about 0.5% (w/w) to about 20% (w/w) of carvone, about 0.5% (w/w) to about 10% (w/w) of carvone, about 0.5% (w/w) to about 5% (w/w) of carvone, about 1% (w/w) to about 50% (w/w) of carvone, about 1% (w/w) to about 40% (w/w) of carvone, about 1% (w/w) to about 30% (w/w) of carvone, about 1% (w/w) to about 20% (w/w) of carvone, about 1% (w/w) to about 10% (w/w) of carvone, about 5% (w/w) to about 50% (w/w), about 5% (w/w) to about 40% (w/w), about 5% (w/w) to about 30% (w/w), about 5% (w/w) to about 20% (w/w), about 5% (w/w) to about 10% (w/w), about 10% (w/w) to about 50% (w/w), about 10% (w/w) to about 40% (w/w), about 10% (w/w) to about 30% (w/w), about 10% (w/w) to about 20% (w/w), about 20% (w/w) to about 50% (w/w), about 20% (w/w) to about 40% (w/w) or about 20% (w/w) to about 30% (w/w). In one embodiment, the composition is from *M. aquatica* var. citrata Lime Mint essential oil. In a further embodiment, the composition comprises about 42.19% (w/w) of limonene and about 16.02% (w/w) of carvone.

In some embodiments, the essential oil composition comprises an essential oil from *M. aquatica* var. Kenting Water Mint and an essential oil from *M. aquatica* var. citrata Lime Mint.

In one embodiment, the skin carcinogenesis is the development of melanoma, basal cell carcinoma (BCC), squamous cell carcinoma (SCC) or keratoacanthoma (KA). In a further embodiment, the squamous cell carcinoma is induced by PLX.

In one embodiment, the skin carcinogenesis is a two-stage skin carcinogenesis. In a further embodiment, the skin carcinogenesis is a drug-promoted two-stage skin carcinogenesis. In a further embodiment, the drug is BRAF-inhibitor. In further embodiments, the drug is vemurafenib (PLX4032), 7,12-dimethylbenz[a]anthracene (DMB A) or 12-O-tetradecanoylphorbol-13-acetate (TPA), which cause formation of skin papilloma.

In one embodiment, the essential oil composition or composition can prevent a two-stage skin carcinogenesis.

In one embodiment, the essential oil composition or composition exhibits significant anti-proliferation effects against $HRAS^{Q61L}$ keratinocytes.

In one embodiment, the essential oil composition or composition induces $G_2/M$ cell-cycle arrest and cell apoptosis.

In one embodiment, the essential oil composition or composition inhibits migratory and invasive abilities of $HRAS^{Q61L}$ keratinocytes.

In one embodiment, the essential oil composition or composition inhibits papilloma formation.

In one embodiment, the essential oil composition or composition diminishes reactivation of MAPK signaling.

In another aspect, the present disclosure provides an essential oil composition comprising one or more essential oil from M. aquatica.

In one aspect, the present disclosure provides a method for whitening skin or reducing skin pigmentation, comprising topically applying to skin an essential oil composition comprising one or more essential oil from M. aquatica, or a composition comprising limonene and carvone and optional one or more essential oil from M. aquatica.

In another aspect, the present disclosure provides a composition comprising limonene and carvone and optional one or more essential oil from M. aquatica.

In some embodiments, the essential oil composition or composition can further comprise one or more additional dermatologically acceptable excipients. Exemplary additional dermatologically acceptable excipients include, but are not limited to, a pH adjusting agent, a chelating agent, a preservative, a co-solvent, a penetration enhancer, a humectant, a thickening or gelling or viscosity building agent, a fragrance, a colorant, and mixtures thereof.

BRIEF DESCRIPTION OF THE DRAWINGS

FIG. 15 shows the experimental design of the two-stage skin carcinogenesis study.

DETAILED DESCRIPTION OF THE INVENTION

Figure 1A:
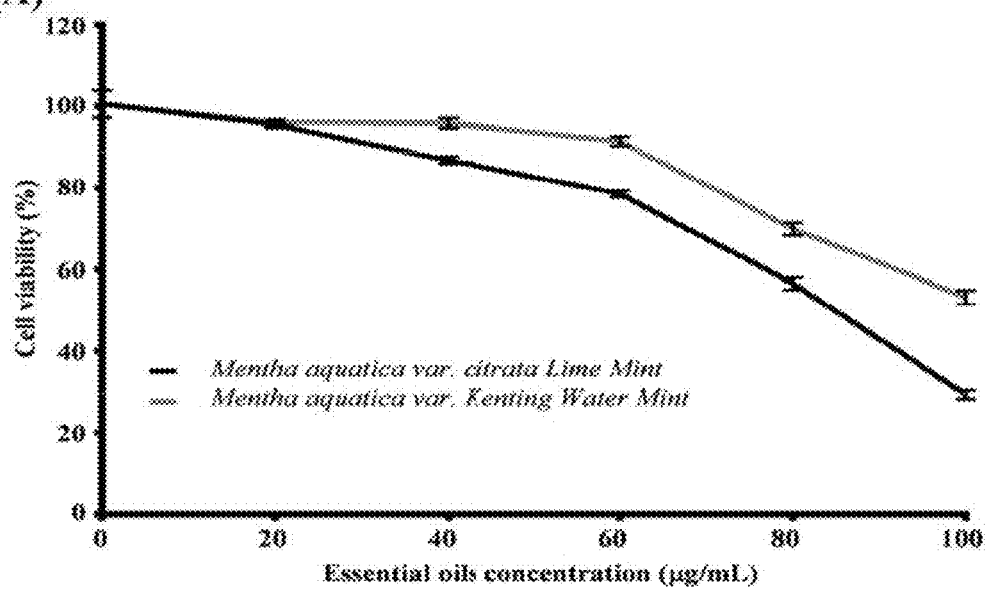
FIGS. 1(A) and (B) show the effect of mint essential oils and compounds in combination on the cell viability of PDV cells. (A) PDV cells were treated with two Mentha species of essential oils at concentrations ranging from 0 to 100 μg/mL for 24 h. Cell viabilities were determined by MTT assay. (B) PDV cells were co-treated with limonene and carvone, major compounds of M. aquatica var. citrata Lime Mint essential oil, at different concentration ranging from 0 to 100 μg/mL. Cell viabilities were detected by MTT assay. Vehicle controls were obtained from cells treated with 0.5% DMSO. The data are representative of three independent experiments and are expressed as mean±SD.

The entire document is intended to be related as a unified disclosure, and it should be understood that all combinations of features described herein are contemplated, even if the combination of features are not found together in the same sentence, or paragraph, or section of this document. The present disclosure as illustratively described in the following may suitably be practiced in the absence of any element or elements, limitation or limitations, not specifically disclosed herein.

Technical terms are used by their common sense unless indicated otherwise. If a specific meaning is conveyed to certain terms, definitions of terms will be given in the following in the context of which the terms are used.

The singular forms "a", "an", and "the" may refer to plural articles unless specifically stated otherwise.

The term "essential oils" refers to volatile liquids extracted from plant material. Essential oils are often concentrated hydrophobic liquids containing volatile compounds. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). Essential oils are insoluble in water and are soluble in alcohol, ether, fixed oils (vegetal), and other organic solvents.

The terms "inhibiting" or "reducing" or any variation of these terms includes any measurable decrease or complete inhibition to achieve a desired result. The terms "promote"

or "increase" or any variation of these terms includes any measurable increase or production of a protein or molecule to achieve a desired result.

The term "effective amount" is the amount necessary to achieve a specific effect, in accordance with what one of ordinary skill in the art would be readily able to determine through routine experimentation.

The term "topical application" means to apply or spread a composition onto the surface of lips or keratinous tissue.

The term "preventing" or any variation of this term means to slow, stop, or reverse progression toward a result. The prevention may be any slowing of the progression toward the result.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus, the compounds, compositions and methods of the present invention may be used for instance as therapeutic treatment over a period of time as well as for chronic therapy.

The term "prevention" and "preventing" comprise a prophylactic treatment, i.e. a treatment of patients at risk to develop a condition mentioned hereinbefore, thus reducing said risk.

Mechanism of Cutaneous Side Effects Induced by BRAF Inhibitors

BRAF (v-raf murine sarcoma viral homolog B1) is a member of the RAF kinase family regulated serine/threonine-specific signal transduction proteins kinases, which are involved in cell division, differentiation and secretion. The BRAF inhibitor, vemurafenib, is a type I BRAF inhibitor which binds with the protein kinase in its active conformation by forming 1-3 hydrogen bonds. Vemurafenib, also known as PLX4032, has been demonstrated to benefit tumor response rate and overall survival in $BRAF^{V600E}$ mutant melanoma patients. The mechanism of action of PLX4032 against tumors is associated with inhibition of the phosphorylation of the oncogenic mitogen-activated protein kinase (MAPK) pathway, a downstream effector of BRAF kinase.

Squamous cell carcinoma (SCC) and keratoacanthoma (KA) develop in approximately 20-30% of patients who are treated with PLX4032. In a recent study, cuSCC and/or KAs emerging from patients administrated with BRAF inhibitor were subjected to analysis of oncogenic mutations. Among them, $HRAS^{Q61L}$ was the most prevalent. Thus, $HRAS^{Q61L}$ was selected to investigate the mechanisms pre-clinically (Fei Su, Amaya Viros, Carla Milagre, et al., *RAS mutations in cutaneous squamous-cell carcinomas in patients treated with BRAF inhibitors. The New England Journal of Medicine,* 2012. 366(3): p. 207-215). Functional studies have demonstrated that these serious side effects are caused by paradoxical MAPK activation. The paradoxical activation of MAPK pathway of wild-type BRAF cell lines bearing either oncogenic RAS mutations or upstream receptor tyrosine kinase activity was observed during treatment with PLX4032. The phenomenon is driven by RAS-independent RAF dimerization, as evidenced by observation that BRAF mutants with impaired kinase activity can still dimerize with CRAF and consequently RAS-independent MAPK signaling hyperactivation (Fei Su, Amaya Viros, Carla Milagre, et al., *RAS mutations in cutaneous squamous-cell carcinomas in patients treated with BRAF inhibitors. The New England Journal of Medicine,* 2012. 366(3): p. 207-215).

Two-Stage Skin Carcinogenesis Mouse Model

The mouse skin model of multiple-stage chemical carcinogenesis is an in vivo model for understanding the development of cutaneous squamous cell carcinoma. The two-stage mechanism of carcinogenesis was first proposed by Berenblum and Shubik in 1947. Topical exposure of carcinogen 7,12-dimethyl[a]anthracene (DMBA), as a tumor initiator results in $HRAS^{Q61L}$ mutation in the mouse skin. Subsequently topical treatment of tumor promoter, 12-O-tetradecanoyl-phorbol-13-acetate (TPA), then leads to the formation of lesions, KAs and the development of SCC. The advantage of the chemical induced two-stage skin carcinogenesis model is that tumor progression involved initiation and promotion stages in mouse dorsal skin throughout the life span can be obviously observed and the time period of the long-term carcinogenetic test reduces (Erika L Abel, Joe M Angel, Kaoru Kiguchi, et al., *Multistage chemical carcinogenesis in mouse skin: fundamentals and applications. Nature Protocols,* 2009. 4(9): p. 1350-1362). Previous study demonstrated that FVB mice administrated with DMBA/TPA along with BRAF inhibitor, PLX4720, show a remarkable acceleration in the appearance of lesions, an increase in incidence, and enhanced progression to KAs and SCC which resemble the papillomas induced by BRAF inhibitors in the clinic (Fei Su, Amaya Viros, Carla Milagre, et al., *RAS mutations in cutaneous squamous-cell carcinomas in patients treated with BRAF inhibitors. The New England Journal of Medicine,* 2012. 366(3): p. 207-215). Tumor development is correlated to proliferation and expansion of not only cancer cells but also stroma, vessels and infiltrating inflammatory elements. The participation of inflammation plays an important part in the progression of cancer. Acute inflammatory responses are regarded as a defensive reaction that eliminates pathogens; however, acute inflammatory responses which evolve into chronic inflammatory responses have been associated with tumor initiation. Neoplastic growth is related to a prolonged inflammatory condition by extrinsic or intrinsic pathways. The former is related with a continued inflammatory condition. The latter is stimulated by genetic transformations which result in activation of oncogenes or inactivation of tumor suppressor genes. Cells with an altered phenotype propagate the secretion of inflammatory mediators thus triggering the formation of the tumor microenvironment (TME) and development of tumors.

Chronic Inflammation and the Tumor Microenvironment

The tumor microenvironment comprises the extracellular matrix as well as myofibroblasts and cellular players, such as fibroblasts, neuroendocrine cells, adipose cells, immune cells, bone marrow-derived inflammatory cells, lymphocytes and the blood vascular networks. Immune-inflammatory cells have been reported to have a crucial role in the early stage of neoplasia. Macrophages have been identified as critical contributors to malignancies in various tumor types, such as melanoma, lung carcinoma, glioma, gastric cancer and wound-induced skin cancer. Tumor-associated macrophages (TAM) presenting in the microenvironment of solid tumor are divided into two subtypes: classicallyactivated macrophages (M1) and alternatively-activated macrophages (M2) depending on different macrophage polarization. M1 macrophages undergoing classical activation by interferon-γ (IFNγ) with either lipopolysaccharide (LPS) or tumor necrosis factor (TNF) have pro-inflammatory and cytotoxic activities. On the other hand, M2 macrophages bearing alternative activation by interleukin-4 (IL-4) are anti-inflammatory, immunosuppressive and promote wound-healing. In response to signals from TME, macrophages show remarkable plasticity and can differentiate into cells of diverse lineages. Therefore, the macrophage polarization affected by TME is a very important target for developing novel therapeutic agents in cancers.

Numerous studies demonstrated that essential oils (EOs) of the *Mentha* species show antiviral, antimicrobial, antioxidant, anti-inflammation and anti-tumor activities. *Mentha piperita* L. EO at 150 µg/mL showed in vitro antimicrobial effect against *S. aureus* and anti-proliferative activity against melanoma cells (A375) and breast cancer cells (MDA-MD-231) (Ersilia Alexa, Corina Danciu, Isidora Radulov, et al., *Phytochemical screening and biological activity of Mentha x piperita L. and Lavandula angustifolia Mill. extracts. Analytical Cellular Pathology* 2018. 2018). *Mentha piperita* L. EO was also demonstrated to possess a protective effect against hepatotoxicity and $CCL_4$-induced liver fibrosis in rats (50 mg/kg, intraperitoneal injection) by improvement of liver injury markers, lipid peroxidation and antioxidant capacity. In another article, Peppermint (*M. piperita* L.) and chocolate mint (*M. piperita* L.) were demonstrated to have antimicrobial activity against *E. coli, S. aureus* and *P. aeruginosa*, antioxidant properties, scavenging nitric oxide (NO) radical activity and anti-inflammatory activity (Mei-Lin Tsai, Chin-Tung Wu, Tsen-Fang Lin, et al., *Chemical composition and biological properties of essential oils of two mint species. Tropical Journal of Pharmaceutical Research,* 2013. 12(4): p. 577-582).

The present disclosure surprisingly found that mint essential oils possess cancer chemoprevention activity and can prevent drug-induced cutaneous side effects. The present disclosure found two essential oils from *M. aquatica* var. Kenting Water Mint (designated KWM-EO) and *M. aquatica* var. Citrata Lime Mint (designated LM-EO) which exhibit significant anti-proliferation effects against keratinocyte bearing $HRAS^{Q61L}$ mutation cell line. The bioactivity of the combination of two major compounds present in LM-EO, i.e., limonene and carvone (designated L+C) is also evaluated. KWM-EO, LM-EO and L+C decrease colony formation, and induced $G_2$/M cell-cycle arrest and cell apoptosis. The present disclosure further investigates the in vivo bioefficacy of both EOs and L+C combination treatments in the two-stage skin carcinogenesis. Overall, the present disclosure demonstrates the novel cancer chemopreventive effect of essential oils from *M. aquatica* var. Kenting Water Mint and *M. aquatica* var. citrata Lime Mint and the combination of limonene and carvone that also have great potential to prevent the cutaneous side effects induced by drug.

Accordingly, the present disclosure provides a method for inhibiting $HRAS^{Q61L}$ mutant keratinocyte activity or treat and/or prevent skin carcinogenesis, comprising topically applying to skin an essential oil composition comprising one or more essential oil from *M. aquatica*, or a composition comprising limonene and carvone and optional one or more essential oil from *M. aquatica*.

*Mentha aquatica* (water mint; *Mentha hirsuta* Huds.) is a perennial flowering plant in the mint family Lamiaceae. *M. aquatica* var. Kenting Water Mint or *M. aquatica* var. citrata Lime Mint are preferred embodiments of the present disclosure.

The essential oil composition used in the method of the present disclosure is topically applied in an amount ranging from about 1 mg to 10 mg/site. In one embodiment, the essential oil composition is topically applied in an amount of about 5 mg/site.

In the composition comprising limonene and carvone and optional one or more essential oil from *M. aquatica*, about 15% (w/w) to 70% (w/w) of limonene and about 5% (w/w) to 50% (w/w) of carvone are used. In one embodiment, the composition is from *M. aquatica* var. citrata Lime Mint essential oil. In a further embodiment, the composition comprises about 42.19% (w/w) of limonene and about 16.02% (w/w) of carvone.

The essential oil composition comprises an essential oil from *M. aquatica* var. Kenting Water Mint and an essential oil from *M. aquatica* var. citrata Lime Mint.

The skin carcinogesis is the development of melanoma, basal cell carcinoma (BCC), squamous cell carcinoma (SCC) or keratoacanthoma (KA). In a further embodiment, the squamous cell carcinoma is induced by PLX. The skin carcinogenesis is a two-stage skin carcinogenesis; particularly, a drug-promoted two-stage skin carcinogenesis. In an embodiment, the drug is BRAF-inhibitor, such as vemurafenib (PLX4032), which promote formation of skin papilloma.

In one embodiment, the essential oil composition or composition can prevent a two-stage skin carcinogenesis. The essential oil composition or composition exhibits significant anti-proliferation effects against $HRAS^{Q61L}$ keratinocytes and induces $G_2$/M cell-cycle arrest and cell apoptosis. Accordingly, the essential oil composition or composition inhibits migratory and invasive abilities of $HRAS^{Q61L}$ keratinocytes and inhibits papilloma formation.

Also, the essential oil composition or composition diminishes reactivation of MAPK signaling.

The present disclosure also found that the essential oil of *M. aquatica* var. citrata Lime Mint has the depigmentation or anti-melanogenesis activity. Accordingly, the present disclosure provides a method for whitening skin or reducing skin pigmentation, comprising topically applying to skin an essential oil composition comprising one or more essential oil from *M. aquatica*, or a composition comprising limonene and carvone and optional one or more essential oil from *M. aquatica*.

The present disclosure further provides an essential oil composition comprising one or more essential oil from *M. aquatica*. Moreover, the present disclosure provides a composition comprising limonene and carvone and optional one or more essential oil from *M. aquatica*.

The essential oil composition or composition can further comprise one or more additional dermatologically acceptable excipients. Exemplary additional dermatologically acceptable excipients include, but are not limited to, a pH adjusting agent, a chelating agent, a preservative, a co-solvent, a penetration enhancer, a humectant, a thickening or gelling or viscosity building agent, a fragrance, a colorant, and mixtures thereof.

An essential oil composition or composition can further comprise one or more emulsifiers. An essential oil fraction can be combined with an emulsifier and a dry carrier, or alternatively an essential oil fraction can be combined with an emulsifier and a liquid carrier, as disclosed above, to form an emulsion. One or more emulsifiers can be used to form an emulsion. In some embodiments, one or more emulsifiers can additionally or alternatively be used as a stabilizer. Stabilizers can be used to alter the viscosity of an emulsion. Altering a viscosity can include maintaining a viscosity, increasing a viscosity, or decreasing a viscosity. A suitable emulsifier can be an emulsifier capable of achieving a threshold droplet size.

In an embodiment, the emulsion is an oil-in-water emulsion. In another embodiment, the emulsion is a water-in-oil emulsion. Suitably, the emulsion may be formulated as a cream. The cream may be an oil-in-water cream or a water-in-oil cream. In one particular embodiment, the cream is an oil-in-water cream. In another embodiment, the emulsion may be formulated as a lotion. The lotion may be an oil-in-water lotion or a water-in-oil lotion.

In one embodiment, the essential oil composition or composition is an ointment. In one embodiment, it may be an oleaginous ointment, an emulsifiable ointment base, and emulsion ointment base and a water-soluble ointment base. Emulsion ointment bases are actually w/o and o/w type of products. They both permit the incorporation of some additional amounts of water without reducing the consistency of the base below that of a soft cream. A w/o emulsion can be diluted with oils. The ointments may also comprise at least one dermatologically acceptable excipient such as a co-solvent, a humectant, a chelating agent, an antioxidant, a preservative, a fragrance, a colorant or a penetration enhancer, or a combination or mixture thereof.

The essential oil composition or composition may further comprise a gelling agent. In an embodiment, the gelling agent is a mixture of two or more gelling agents. Exemplary gelling agents include, but are not limited to, agar, alginate, arabinoxylan, carrageenan, carboxymethylcellulose, hydroxyethylcellulose, hydroxypropylcellulose, hydroxypropyl methylcellulose, cellulose, curdlan, gelatin, gellan, beta-glucan, tragacanth gum, guar gum, gum arabic, locust bean gum, pectin, starch, a carbomer, acrylate copolymers, silica, xanthan gum, salts thereof, or a combination or mixture thereof.

It will be readily apparent to those skilled in the art that the compositions and methods described herein may be modified and substitutions may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLE

Materials and Methods

Chemicals and Reagents

Dimethyl sulphoxide (DMSO), (R)-(-)-carvone, 3-(4,5-dimethylthiazol-2-yl)-2,5-diphenyltetrazolium bromide (MTT), lipopolysaccharide (LPS), propidium iodide (PI), polyoxyethylene octyl phenyl ether (Triton X-100), hydrogen peroxide ($H_2O_2$), radio-immunoprecipitation assay (RIPA), $Na_3VO_4$, phenylmethanesulfonyl fluoride (PMSF), ammonium persulfate (APS), TEMED, skimmed milk, 7,12-dimethylbenz[a]anthracene (DMBA), 12-O-tetradecanoylphorbol-13-acatate (TPA), $NaHCO_3$, HEPEs, crystal violet, glycerol gelatin, polyethylene glycol 300 (PEG300) and polysorbate (Tween20) were purchased from Sigma-Aldrich Corporation (Missouri, United States). (+)-Limonene and acetone were purchased from Acros Organic (Belgium). Acrylamine/bis solution (30%) was purchased from Bio-Rad (California, United States). Matrigel matrix was purchased from BD Bioscience (California, United States). Selumetinib (AZD6244) and vemurafenib (PLX4032) were purchased from Medkoo Biosciences (North Carolina, United States). Dulbecco's Modified Eagle Medium (DMEM), antibiotic mixture (penicillin/streptomycin), trypsin, pluronic F68, 4',6-diamidino-2-phenylindole (DAPI) were purchased from Invitrogen (Massachusetts, United States). Fetal bovine serum (FBS) was purchased from GE Healthcare (Illinois, United States). Griess reagents were purchased from Cayman Chemical (Michigan, United States). Bovine serum albumin (BSA) and glycine were purchased from Alpha Bio-chemistry (Texas, United States). RNase A, 3,3'-diaminobenzidine tetrahydrochloride (DAB) and goat anti-rabbit IgG (H+L) Cross-Adsorbed were purchased from Thermo Fisher Scientific (Massachusetts, United States). Hemotocylin and eosin (H&E), formalin and xylene were purchased from MUTO Pure Chemicals (Tokyo, Japan). Universal Immuno-peroxidase Polymer was purchased from Nichirei Bioscience (Tokyo, Japan). Paraffin was purchased from Leica Biosystems (Wetzlar, Germany). PBS, TBS, Tris-Glycine SDS Running Buffer, Western Transfer Buffer, 1 M Tris pH 6.8 and 1.5 M Tris pH 8.8 were purchased from Omics Bio (Taipei, Taiwan).

Primary antibodies including ERK 1, wee1, cyclin B1, cdc2 p34, p-cdc2 p34, PARP-1 and cytokeratin 14 (K14) were purchased from Santa Cruz (Texas, United States). Antibodies including phospho-p44/42 MAPK (Erk1/2), MEK1/2 and phospho-MEK1/2 were purchased from Cell Signaling Technology (Massachusetts, United States). Antibodies including ras and Ki67 were purchased from Abcam (Cambridge, United Kingdom). Caspase-3 antibody was purchased from GeneTex (Texas, United States).

Mint Cultivation and Distillation of Essential Oils

Two varieties of *Mentha aquatica* (Lamiaceae), namely *M. aquatica* var. Kenting Water Mint and *M. aquatica* var. Citrata Lime Mint were cultivated in the experimental field for 2 years. Mature shoots were harvested and subjected to water vapor distillation to collect essential oils. Two kg of fresh shoots from each variety were distilled with 4 liters of water. Mint essential oil was evaporated, passed through a condenser then the oil and hydrosol were collected with a separating funnel. After 1 liter of the hydrosol/essential oils was collected, the distillation was ended. The hydrosol and essential oil were then separately collected for the use in the experiments described herein. The mint essential oils were stored at −20° C. in sealed vials. Essential oils used in in vitro cell-based assays were diluted into different concentrations with DMSO and those used in in vivo animal studies were diluted in acetone.

Cell Lines and Cell Culture

PDV cells, which harbor the $HRAS^{Q61L}$ mutation were obtained from CLS Cell Lines Service (Eppelheim, Germany). RAW 264.7 macrophage cells were obtained from the American Type Culture Collection (ATCC, Virginia, United States). Cells were cultured at 37° C. in DMEM supplemented with 10% FBS, containing 100 units/mL penicillin and 100 μg/mL streptomycin in a humidified 5% $CO_2$ incubator. Cells were used within 10 passages for this study.

Measurement of PDV Cell Viability

Cells were seeded in 96-well plates at a density of $5×10^3$ for 16 h and treated EOs or compounds for 24 h. Cell proliferation was determined by MTT-based colorimetric assays according to Scudiero et al. The viability of the cells treated with vehicle-only (0.5% DMSO) was defined as 100% viable. The viability of the cells after treatment with EOs or compounds was calculated using the following formula: cell viability (%)=[$OD_{570}$(treated cells)/$OD_{570}$(vehicle control)]×100.

Measurement of Nitric Oxide Production in RAW 264.7 Cells

RAW 264.7 cells, a murine macrophage cell line, were seeded in 96-well plates at a density of 2×10$^5$ cells/well for 1 h. The cells were pre-treated with EOs at concentrations ranging from 0 to 100 μg/mL for 1 h and then incubated with or without 1 μg/mL of LPS for 24 h. A stable oxidative end product of NO, nitrite $NO^{2-}$, accumulation in the medium was determined by the Griess reagent (Cayman, United States). Briefly, 80 μL supernatants were reacted with 40 μL Griess reagent R1 and 40 μL Griess reagent R2 in 96-well plates for 30 minutes, and absorbance was detected at 540 nm using an ELISA reader. Besides nitrite content, cell viabilities of macrophages were also examined by MTT-based colorimetric assay. NO inhibition (%)={$OD_{540}$ (LPS group)−[$OD_{540}$ (EOs treated group)−$OD_{540}$ (blank)]/$OD_{540}$ (LPS group)}×100.

Colony-Formation Assay

Colony formation was obtained by growing PDV cells 250 cells/well in 24-well plates with the indicated EO or compound concentrations for 6 days. The culture medium was refreshed once at day 3. Cells were fixed with chilled methanol and stained with 0.1% crystal violet. Cells-retaining crystal violet were dissolved with 20% acetic acid and quantified by measuring absorbance at 595 nm. The relative colony-forming percentage in each treatment was compared with the vehicle-control treatment.

Cell Invasion Assay

The cell invasion assay was performed by Millicell Cell Culture Inserts (Merck Millipore, United States). For invasion assay, 100 μL Matrigel (300 μg/mL) was applied to 8-mm polycarbonate membrane filter and incubated in 37° C. for 2 h. PDV cells (5×10$^4$) were seeded to Matrigel-coated filters in 200 μL of serum-free medium in triplicate for 16 h. The bottom chamber of the apparatus contained 1 mL medium with 10% FBS as a chemoattractant and the indicated concentrations of EOs or compounds. Cells were allowed to migrate for 24 h at 37° C. After incubation for 24 h, the non-migrated cells on the apical side of the membrane were removed with cotton swabs. The migrated cells on the basal side of the membrane were fixed with cold 100% methanol for 20 min and washed 3 times with PBS. The cells were stained with 0.1% crystal violet and then washed with PBS to remove extra dye solution. Images were captured using a reverse-phase microscope (Zeiss Axiovert 200M). Cells retaining crystal violet were dissolved with 20% acetic acid and quantified by measuring absorbance at 595 nm.

Wound Healing Assay

The wound healing assay was performed by using Culture-Insert (ibidi GmbH, Germany). Culture-Inserts were inserted in 24-well plates before cells were seeded. PDV cells were seeded in Culture-Inserts at a density of 5×10$^5$ cells/mL in 70 μL medium. After 16 h, Culture-Inserts were removed which created two cell-free gaps of 500±50 Undetached cells were washed away by PBS, then the remaining attached cells were immersed in 1 mL medium with or without EOs or compounds. Cell migration was observed using a reverse-phase microscope (Zeiss Observer D1) every 6 h.

Cell-Cycle Analysis

PDV cells were seeded in 6-well plates at a density of 1×10$^5$ cells/well with respective medium containing 10% FBS for 16 h. To synchronize the cell cycle, cells were washed with PBS and incubated with fresh medium containing 5% FBS for 8 h, followed by washing with PBS and incubating with fresh medium containing 0.5% FBS for 24 h. Then the cell culture was incubated with medium containing 10% FBS and EOs or compounds at the indicated time points. Both adherent and floating cells were collected, washed with PBS, and fixed with 500 μL ice cold 70% ethanol overnight at 4° C. Cells were stained with 500 μL propidium iodide solution, which contained 20 μg/mL PI, 20 μg/mL RAase A, 0.1% Triton X-100 for 30 min at room temperature in the dark and then analyzed by flow cytometry (Flow cytometry BD Accuri C6, United States).

Apoptosis Assay

Cells were seeded in 6-well plates at density of 1.5×10$^5$ cells/well for 16 h and treated with EOs or compounds. After 24 h, both adherent and floating cells were collected and washed with PBS. Apoptotic cells were analyzed by using FITC Annexin V Apoptosis Detection Kit (BD Bioscience, United States) according to the manufacturer's instructions. In short, PDV cells were suspended in 500 μL 1 X Annexin V Binding Buffer and co-stained with FITC Annexin V and propidium iodide for 15 min at room temperature in the dark. The fluorescence-binding cells were analyzed by flow cytometry. Cells that stain FITC Annexin V and PI for (+/−) are undergoing apoptosis. Cells that stain FITC Annexin V and PI for (+/+) are either in the end stage of apoptosis, are undergoing necrosis, or are already dead.

Western Blot Analysis

Cells were treated with EOs or compounds at the indicated concentrations and lysed in RIPA lysis buffer. Protein concentrations were measured by DC protein assay (Bio-Rad, United States). Western blotting was performed as described by Shyur et al. Protein samples were separated by 10 or 12% SDS-PAGE, and electro-transferred onto PVDF membranes (Merck Millipore, United States). The membranes were blocked with 5% skimmed milk in TBST for 1 h at room temperature. After washing the membranes three times with TBST, membranes were incubated with appropriate primary antibodies overnight (12-16 h) at 4° C. The membranes were washed with TBST three times, followed by incubation with horseradish peroxidase (HRP)-conjugated anti-mouse IgG or anti-rabbit IgG secondary antibodies for 2 h at room temperature. Reactive protein bands were visualized using enhanced chemiluminescent detection reagents (GE Healthcare, United States) and exposed to chemiluminescence light film (GE Healthcare, United States). The expression levels of targeted proteins were quantified by ImageJ software (National Institutes of Health, United States).

Experimental Animals

Female FVB/NJNarl mice (3 weeks old) were purchased from the National Laboratory Animal Center (Taipei, Taiwan) and bred in the Laboratory Animal Core Facility (Agricultural Biotechnology Research Center, Academia Sinica, Taiwan). Animals were given a standard laboratory diet and distilled $H_2O$ ad libitum and kept on a 12-hour light/dark cycle at 22±2° C. and humidity 55±5%. Animals were acclimatized for 1 week before the experiments were performed.

Two-stage Skin Carcinogenesis Study

The experimental design of this study is summarized in FIG. 15. Female FVB/NJNarl mice (5-6 weeks old) were randomized into 9 groups, each group contained 8 mice. Mice had their back hair shaved three days before topical application of 25 μg 7,12-dimethylbenz[a]anthracene (DMBA) in 200 μL acetone. The first week after tumor initiation, 4 μg of 12-O-tetradecanoylphorbol-13-acatate (TPA) in 200 μL acetone was topically applied twice a week to the shaved back skin for 12 weeks. Mice were treated with the indicated concentrations of mint EOs or compounds (in 200 μL acetone) twice a week by topical application the day after TPA treatment for 12 weeks. Tumor size of more than 1 mm diameter was counted every week. After mice were sacrificed, internal organs (heart, liver, spleen, lung, and kidneys), serum, skin and papillomas were collected and fixed with 10% formalin or stored at −80° C.

Histopathological and Immunohistochemical Analysis

The skin and papilloma tissues were collected after mice were sacrificed. Tissues were then fixed with 10% formalin for one week and embedded in paraffin. Tissue sections were cut at 4 μm thickness, then deparaffinized two times with 100% xylene following rehydration in 100%, 75%, 70%, 50% descendant ethanol bath and a final wash with PBS. The deparaffinized sections were boiled with appropriate pH antigen retrieval buffer and incubated with 3% hydrogen peroxidase for 5 min to decrease non-specific staining. The blocking solution containing 10% BSA and 0.4% Triton X-100 in PBS was added to tissue sections for 1 h. The sections were stained with the indicated primary antibodies at appropriate dilution fold at 4° C. overnight (12-16 h). The slides were treated with Universal Immuno-peroxidase Polymer (Nichirei Bioscience, Japan) and the peroxidase detected site was developed with 3,3'-diaminobenzidine tetrahydrochloride (DAB). Hematoxyline solution was used for counterstaining. The slides were mounted with mounting media (Fisher Scientific, United States) for longer storage. An upright microscope (Carl Zeiss Axio Imager, Z1) was used to observe the expression of targeted proteins.

MTT Assay

The anti-melanoma cell proliferation activity of *M. aquatica* var. Citrata Lime Mint (LM-EO) and Kenting Water Mint essential oil (KWM-EO) were carried by MTT-based colorimetric assay. Murine melanoma B16 cells were treated with LM-EO or KWM-EO for 24 h. Viability of the cells treated with vehicle-only (0.5% DMSO) was defined as 100% viability. Viable cells after treatment with compound was calculated using the following formula: cell viability (%)=[$OD_{570}$ (treated cell culture)/$OD_{570}$ (vehicle control)]× 100.

Depigmentation Assay

B16 cells (1×10$^6$ cells/15-cm dish) were treated with vehicle (0.5% DMSO), 15 and 25 μg/mL LM-EO (LM15 and LM25), or 100 μg/mL kojic acid (KA100) for 6, 12, 24 h. After washing with PBS for two times, the cells were harvested by cell scrapper and centrifugation. The cell pellets were then taken a photo before dissolved in 1 N NaOH at 60° C. for 1 h. The volume of NaOH used to dissolve the cell pellets were adjusted based on the cell populations to yield the equal concentration. The absorbance was then measured at 405 nm.

Statistical Analysis

All the data are expressed as mean±standard deviation (SD). Statistical analyses were conducted by the Predictive Analysis Suite Workstation (PASW Statistics, United States), and the significant difference between different treatment groups was determined by one-way analysis of variance (ANOVA). P values of less than 0.05 were considered statistically significant.

Example 1 Effect on Proliferation of $HRAS^{Q61L}$ Mutant PDV Cells

The PDV cell line is a DMBA-transformed mouse cutaneous squamous cell carcinoma (cuSCC) cell line that carries $HRAS^{Q61L}$ gene mutation. The $HRAS^{Q61L}$ mutant keratinocytes are commonly observed in DMBA/TPA-induced mouse cuSCC. The PDV cell line was selected to investigate the EO effects and underlying mechanisms reflecting two-stage skin carcinogenesis. The effect of the two mint EOs on PDV cell viability was determined by MTT-based colorimetric assays. The data in FIG. 1A show that *M. aquatica* var. citrata Lime Mint EO (designated LM-EO) and *M. aquatica* var. Kenting Water Mint EO (designated KWM-EO) have significant inhibitory activity on PDV cell proliferation with 29.4% and 53.3% cell viabilities at 100 μg/mL.

Figure 1B:
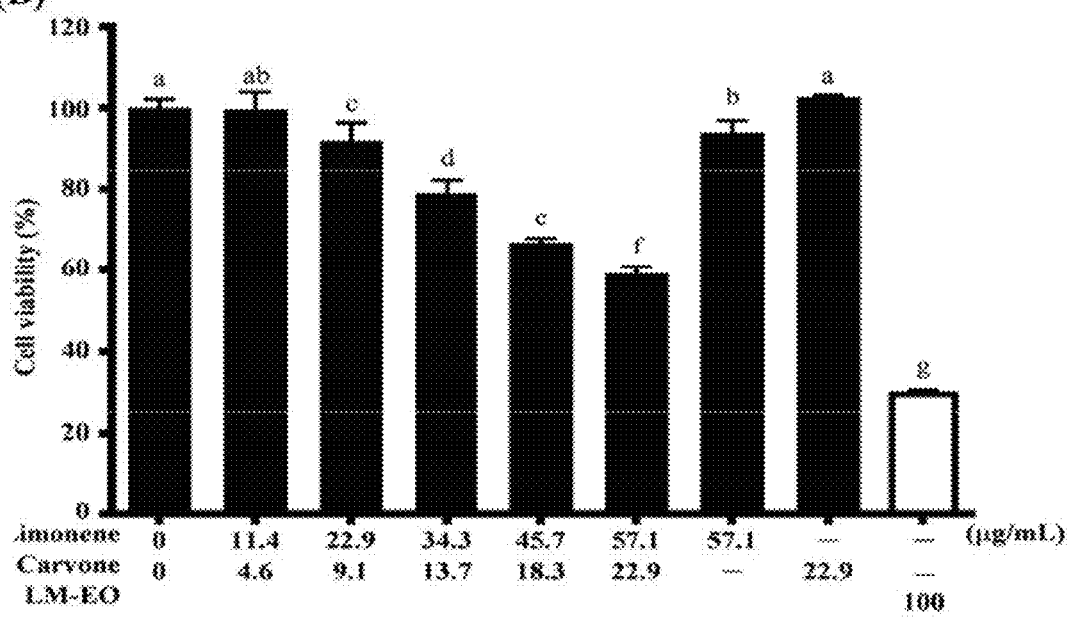

The chemical profiles of LM-EO and KWM-EO were analyzed by GC×GC-TOF MS (Table 1). The data indicated that the most abundant compounds in LM-EO are limonene (relative content 33.11%) and (−)-carvone (relative content 12.57%). Nevertheless, there were no major or dominant compounds with content more than 25% in KWM-EO. The combinational bioactivities of both limonene and (−)-carvone compounds and thus investigated them in parallel. We investigated the anti-PDV cell viability of limonene and (−)-carvone in combination (designated as L+C) using a content ratio of approximately 2.5:1 in the LM-EO, ranging from 0 to 100 μg/mL (FIG. 1B). A concentration-dependent cytotoxicity of L+C was observed at the analyzed concentrations less than 100 μg/mL referred to as LM-EO.

TABLE 1

Chemical constituents of Mentha aquatica var. Lime Mint and Mentha aquatica var. Kenting Water Mint essential oils.

| | | | | | | Relative percentage | |
|---|---|---|---|---|---|---|---|
| Chemical compound | CAS no. | RT1 | RT2 | $KI_{exp}$ | $KI_{Lit}$ | LM | KWM |
| α-Pinene | 7785-70-8 | 6.27 | 0.0245 | 936 | 929 | 6.00 | 10.49 |
| β-Pinene | 127-91-3 | 7.00 | 0.0250 | 981 | 973 | 8.44 | 15.41 |
| β-Myrcene | 123-35-3 | 7.20 | 0.0243 | 992 | 993 | 0.47 | 4.86 |
| β-Cymene | 535-77-3 | 7.73 | 0.0253 | 1027 | 1031 | 2.70 | 3.07 |
| Limonene | 138-86-3 | 7.87 | 0.0240 | 1036 | 1036 | 33.11 | — |
| Eucalyptol | 470-82-6 | 7.93 | 0.0258 | 1040 | 1041 | 7.69 | 12.87 |
| β-Ocimene | 3338-55-4 | 8.07 | 0.0245 | 1049 | 1036 | — | 22.18 |
| Linalool | 78-70-6 | 8.87 | 0.0262 | 1097 | 1101 | — | 0.25 |
| Limonene oxide | 4959-35-7 | 9.53 | 0.0295 | 1142 | 1137 | 2.12 | — |
| Menthone | 89-80-5 | 9.80 | 0.0325 | 1160 | 1154 | 0.04 | 0.04 |
| Menthofuran | 494-90-6 | 9.93 | 0.0267 | 1169 | 1169 | — | 0.04 |
| Levomenthol | 2216-51-5 | 10.07 | 0.0277 | 1178 | 1172 | — | 0.05 |
| Dihydrocarvone | 1478-60-2 | 10.47 | 0.0330 | 1203 | 1200 | 0.33 | — |
| p-Menth-8-en-2-one | 5948-04-9 | 10.60 | 0.0330 | 1213 | 1218 | 0.05 | 0.07 |
| Carveol | 1197-07-5 | 10.73 | 0.0272 | 1222 | 1223 | — | 0.13 |

TABLE 1-continued

Chemical constituents of Mentha aquatica var. Lime Mint and Mentha aquatica var. Kenting Water Mint essential oils.

| Chemical compound | CAS no. | RT1 | RT2 | $KI_{exp}$ | $KI_{Lit}$ | Relative percentage LM | KWM |
|---|---|---|---|---|---|---|---|
| Carvone | 6485-40-1 | 11.13 | 0.0327 | 1251 | 1249 | 12.57 | 1.59 |
| Linalyl acetate | 115-95-7 | 11.20 | 0.0270 | 1256 | 1257 | 0.03 | 0.82 |
| Dihydroedulan I | 63335-66-0 | 11.87 | 0.0258 | 1302 | 1292 | 0.13 | 0.28 |
| β-Bourbonene | 5208-59-3 | 13.13 | 0.0250 | 1396 | 1386 | 0.62 | 0.78 |
| Caryophyllene | 87-44-5 | 13.60 | 0.0258 | 1434 | 1431 | — | 2.80 |
| Humulene | 6753-98-6 | 14.00 | 0.0318 | 1466 | 1465 | — | 0.29 |
| Ethyl 4-ethoxybenzoate | 23676-09-7 | 14.73 | 0.0302 | 1524 | 1521 | 1.99 | 2.37 |
| Viridiflorol | 552-02-3 | 15.73 | 0.0272 | 1680 | 1603 | 2.19 | 3.47 |
| Monoterpene hydrocarbons identified (%) | | | | | | 50.85 | 56.01 |
| Oxygenated monoterpene identified (%) | | | | | | 22.83 | 15.86 |
| Sesquiterpene hydrocarbon identified (%) | | | | | | 0.62 | 3.87 |
| Oxygenated sesquiterpene identified (%) | | | | | | 2.19 | 3.47 |
| Other (%) | | | | | | 2.12 | 2.65 |
| Identified components (%) | | | | | | 78.61 | 81.86 |

Example 2 Mint Essential Oils Inhibit Colony Formation

Figure 2:
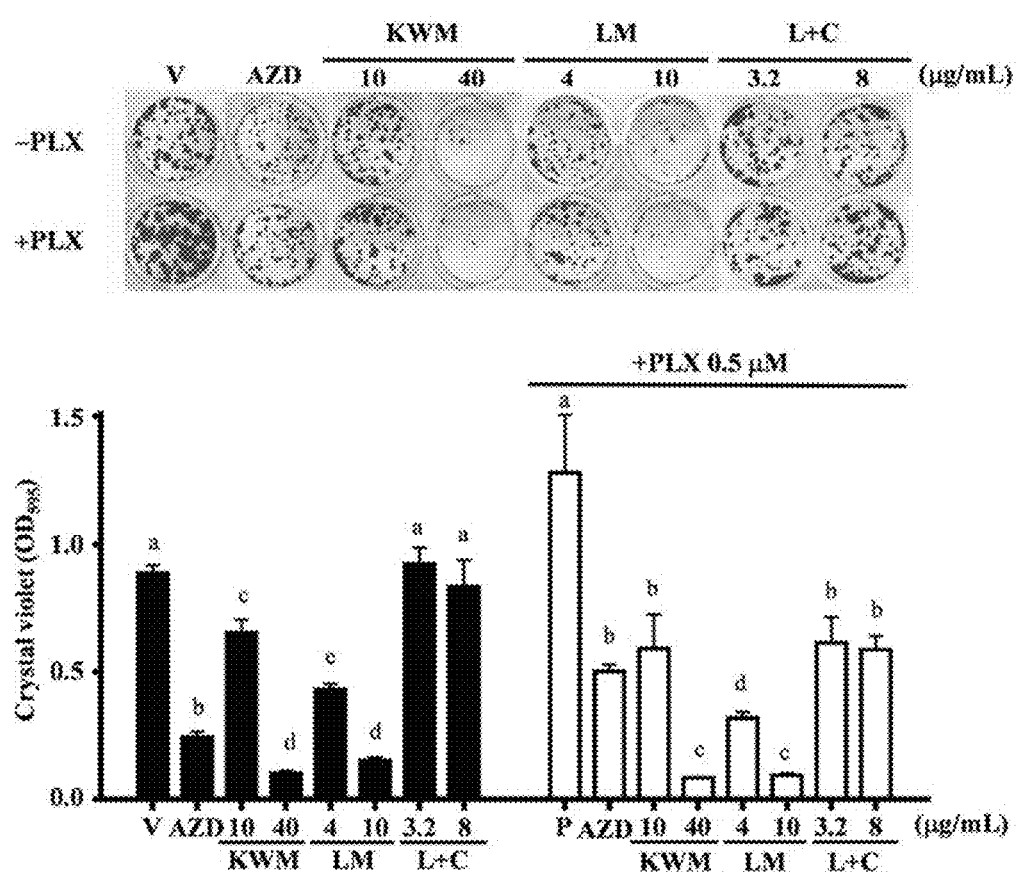
FIG. 2 shows the effect of mint essential oils on colony formation ability of PDV cells in the presence or absence PLX4032. PDV cells were seeded in 24-well plates in triplicate at a density of 250 cells/well and treated with the indicated concentrations of mint essential oils or compounds alone or co-treated with 0.5 μM PLX4032 for 6 days. After fixation, live cells were stained with 0.1% crystal violet for 30 min. Crystal violet was dissolved in 20% acetic acid and the absorbance was detected at $OD_{595}$ nm. Vehicle controls were obtained from cells treated with 0.5% DMSO. The data are representative of three independent experiments and are expressed as mean±SD. V: vehicle, AZD: AZD6244 (MEK inhibitor) 0.5 μM, P: PLX4032 0.5 μM, KWM: Kenting Water Mint, LM: Lime Mint, L+C: Limonene+Carvone.

Colony formation assay was utilized to assess the capability of a single PDV cell growing into a colony with mint EOs of KWM or LM, L+C treatment or co-treated with PLX4032. The MEK inhibitor, AZD6244 was tested in parallel as a positive control. KWM-EO and LM-EO had significant effect on suppressing colony formation ability, but L+C combinational treatment had no effect (FIG. 2). Meanwhile, PLX4032 treatment significantly promoted PDV cell colony formation after treatment for six days. The colony formation ability of PDV cells stimulated by 0.5 μM PLX4032 was diminished by KWM-EO, LM-EO and L+C at tested concentrations. The EO from Lime Mint showed better inhibitory activity than that of KWM-EO. MEK inhibitor at 0.5 μM decreased clonogenic formation ability of PDV cells in the presence or absence of PLX4032.

Figure 3:
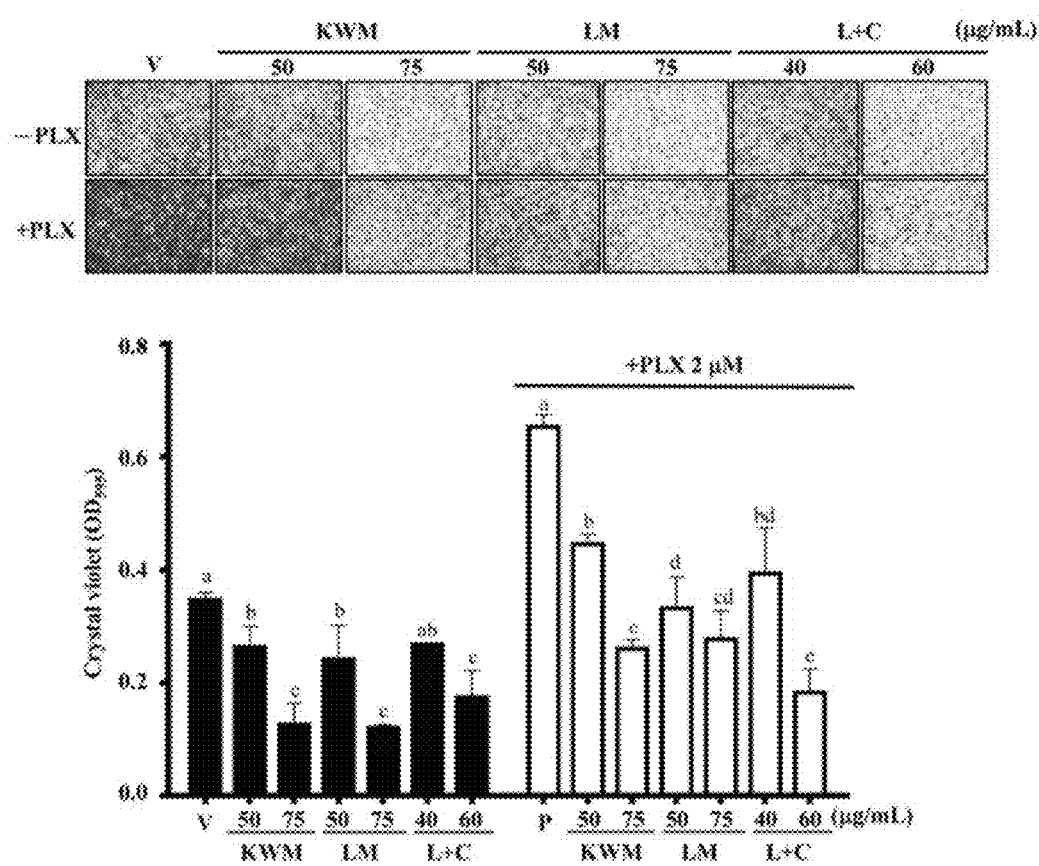
FIG. 3 shows the effect of mint essential oils on cell invasive ability of PDV cells with or without PLX4032-stimulation by transwell invasion assay. PDV cells ($5\times10^4$) were treated with 2 μM PLX4032 and/or indicated concentrations of mint essential oils or compounds for 24 h. Cells on the basal side were stained with 0.1% crystal violet. Cells stained with crystal violet were dissolved in 20% acetic acid and quantified by measuring absorbance at 595 nm. Vehicle controls were obtained from cells treated with 0.5% DMSO. The data are representative of three independent experiments and are expressed as mean±SD. Images were taken by using Carl Zeiss Axiovert 200M microscope (magnification: 200×). V: vehicle, P: PLX4032 2 μM, KWM: Kenting Water Mint, LM: Lime Mint, L+C: Limonene+Carvone.

Example 3 Mint Essential Oils Suppress Migratory and Invasive Ability of PDV Cells Cell migration is a highly-integrated and multi-step process that plays an important role in the progression of late-stage cancer. Cell invasion is involved in extracellular matrix degradation and proteolysis. In the study, wound healing assay and transwell invasion assay were used to examine migratory and invasive abilities of PDV cells, respectively, with or without PLX4032 stimulation. In invasion assay, PLX4032 promoted the invasive ability of PDV cells (FIG. 3). Further, in the presence or absence of PLX4032, KWM-EO, LM-EO and L+C treatment for 24 h reduced invaded cells on concentration-dependence.

Figure 4A:
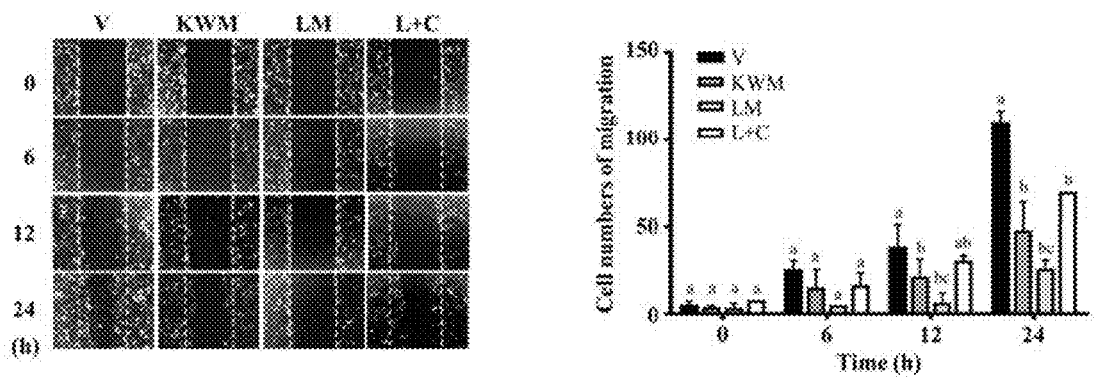
FIGS. 4(A) and (B) show the effect of mint essential oils on cell migratory ability of PDV cells with or without PLX4032-stimulation by wound healing assay. (A) PDV cells were treated with mint essential oils or compounds and observed after 0, 6, 12, 24 h. (B) PDV cells were co-treated with 2 μM PLX4032 and mint essential oils or compounds and observed after 0, 6, 12, 24 h. Migrated cells were quantified by using ImageJ. Vehicle controls were obtained from cells treated with 0.5% DMSO. The data are representative of three independent experiments and are expressed as mean±SD. Mean without a common letter differs, p<0.05. Images were taken by using Carl Zeiss Observer D1 microscope (magnification: 200×). V: vehicle, P: PLX4032 2 μM, KWM: Kenting Water Mint 50 μg/mL, LM: Lime Mint 50 μg/mL, L+C: Limonene+Carvone 40 μg/mL.
Figure 4B:
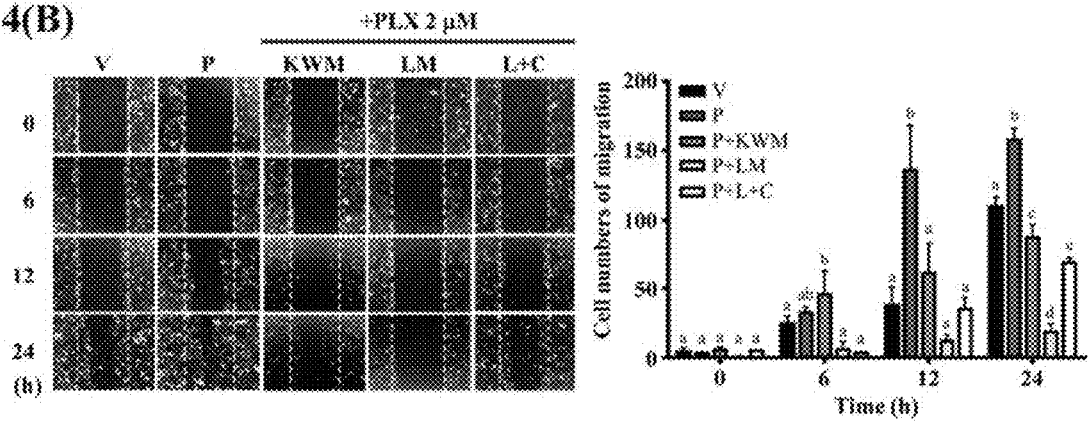

In wound healing assay, 50 μg/mL KWM-EO, 50 μg/mL LM-EO and 40 μg/mL L+C reduced PDV cell migratory ability at 24 h treatment, and LM-EO had a better effect than the others (FIG. 4). On the other hand, 2 μM PLX4032 treatment strongly promoted cell migration of PDV cells within 24 h treatment, KWM-EO, LM-EO and L+C combination, similarly both EOs and compounds only, significantly suppressed PLX4032-stimulated migratory ability of PDV cells.

Example 4 Effect on Cell-Cycle Machinery of PDV Cells

Figure 5A:
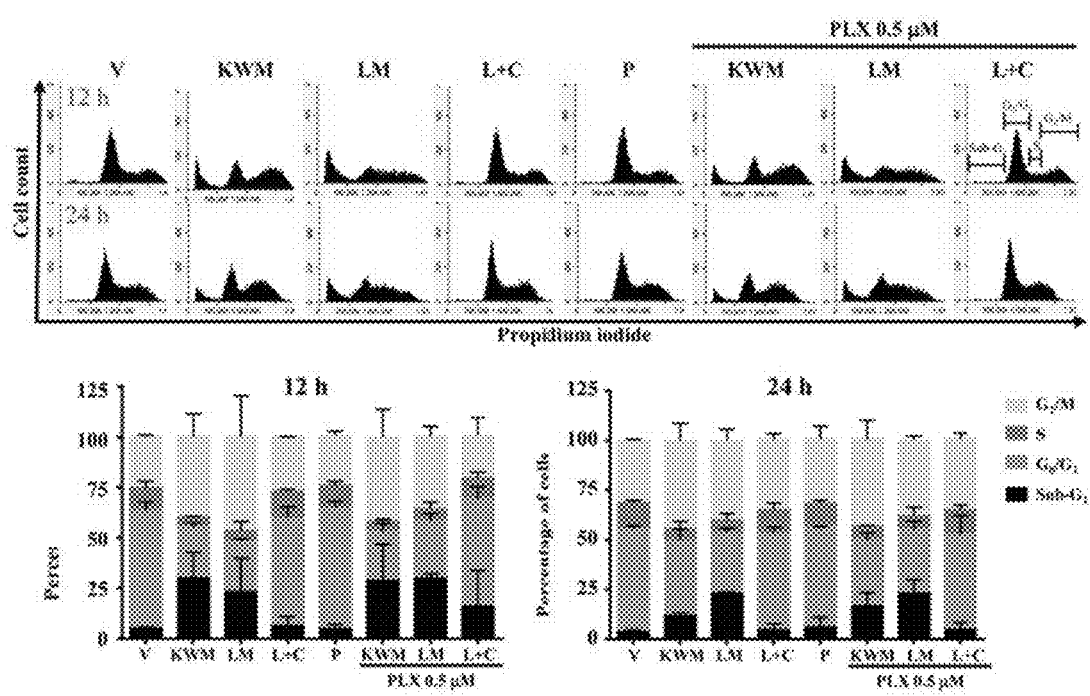
FIGS. 5(A) and (B) show the DNA distribution analysis and western blotting of PDV cells treated with mint essential oils or compounds with or without PLX4032 treatment. (A) PDV cells were synchronized by incubating with gradually decreasing percentage of serum. Then, cells were treated with 0.5 μM PLX4032 and/or indicated concentrations of mint essential oils or compounds for 12, 24 h. Cells were stained with 20 μg/mL propidium iodide for 30 min and analyzed by flow cytometry. The percentage of DNA at sub-$G_1$, $G_0/G_1$, S and $G_2/M$ phases were calculated. (B) PDV cells were synchronized and administrated with 0.5 μM PLX4032 and/or the indicated concentrations of mint essential oils or compounds for 24 h. The cell lysates were collected and p-cdc2 and cdc2 proteins were detected. The ratio of phosphorylated protein to original protein was calculated. Vehicle controls were obtained from cells treated with 0.5% DMSO. The data are representative of three independent experiments and are expressed as mean±SD. V: vehicle, P: PLX4032 0.5 μM, KWM: Kenting Water Mint 75 μg/mL, LM: Lime Mint 75 μg/mL, L+C: Limonene+Carvone 60 μg/mL.

We determined the effect of KWM-EO, LM-EO and a combination of L+C, with or without co-treatment with 0.5 μM PLX4032 on the cell cycle phase of PDV cells (FIG. 5A). When cells were treated with 75 μg/mL KWM-EO for 12 h, $G_0/G_1$ phase DNA was decreased from 58.8% to 25.4%, whereas the $G_2/M$ phase DNA was increased from 25.5% to 40.0%, the apoptotic sub-$G_1$ DNA was increased from 5.1% to 30.1%, compared to the vehicle-treated cells. The $G_0/G_1$ phase DNA in PDV cells treated with 75 μg/mL LM-EO was decreased from 58.8% to 25.0%, whereas the $G_2/M$ phase DNA was increased from 25.5% to 46.8%, and the apoptotic sub-$G_1$ was increased from 5.1% to 23.4%. The cellular DNA distribution in the cell-cycle of PDV cells treated with 60 μg/mL L+C compounds was similar to vehicle control cells. 0.5 μM PLX4032 treatment did not affect cell-cycle DNAs in PDV cells. Co-treatment PLX4032 with EOs or L+C revealed similar cell-cycle DNA distribution in the cells treated with EOs or L+C alone. Taken together, KWM-EO and LM-EO can induce $G_2/M$ arrest in PDV cells after 12-24 h treatment.

Figure 5B:
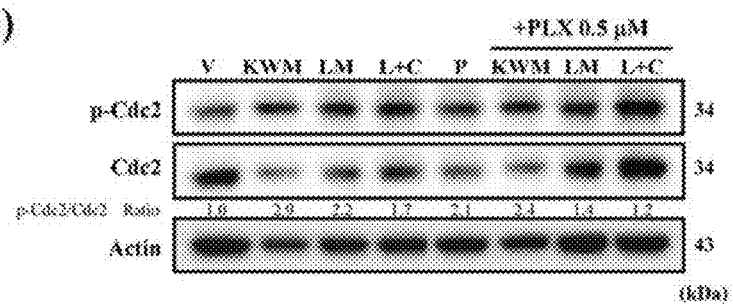

We further investigated the mechanisms underlying $G_2/M$ arrest in PDV cells induced by essential oil treatments. The cell division cycle protein 2 homolog (cdc2) is essential in the cell cycle transition from $G_2$ to M phase, and we examined this protein level in the treated cells. The data in FIG. 5B reveal that PDV cells treated with 75 μg/mL KWM-EO, 75 μg/mL LM-EO and 60 μg/mL L+C for 24 h that increased the ratio of phospho-cdc2 to original cdc2 proteins 2.9-fold, 2.2-fold and 1.7-fold, respectively; while 0.5 μM PLX4032 treatment increased the ratio of p-cdc2/cdc2 2.1-fold compared to vehicle group. When the cells were co-treated with PLX4032 and KWM-EO, LM-EO or L+C that also increased the ratio of p-cdc2/cdc2 2.4-fold, 1.4-fold, 1.2-fold. These results support the flow cytometry data, indicating indeed the specific mint essential oils and L+C can induce PDV cells arrested in $G_2/M$ phase.

Figure 6A:
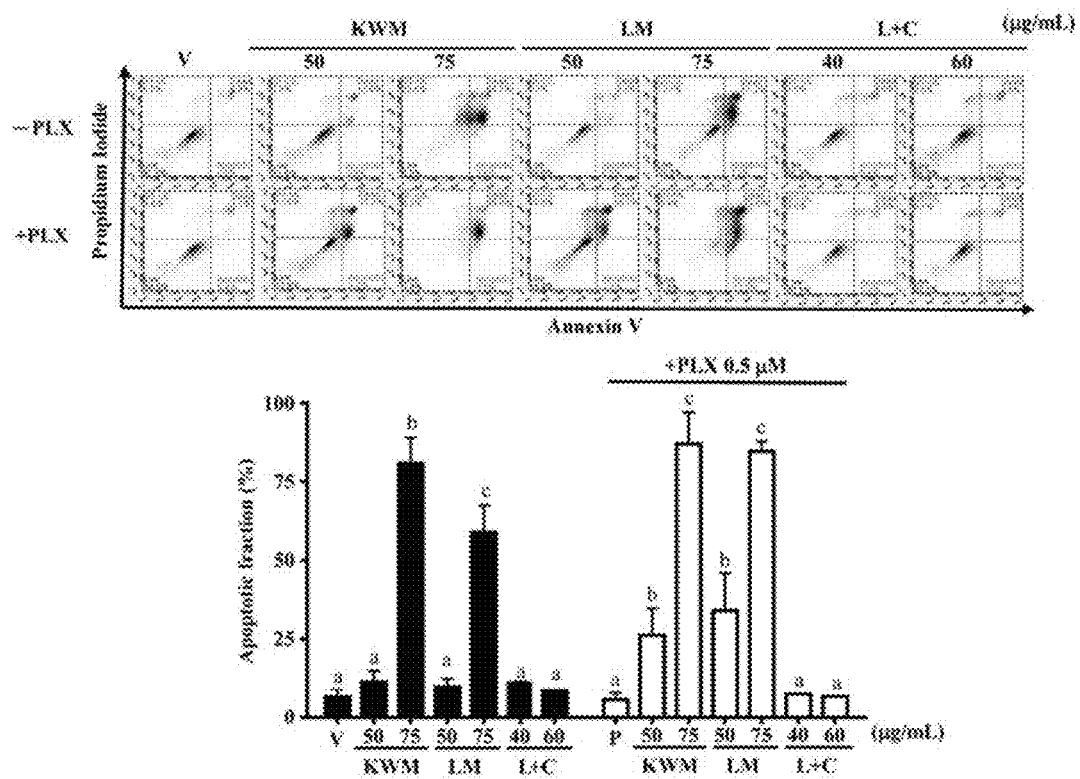
FIGS. 6(A) and (B) show that mint essential oils induced cell apoptosis in PDV cells with or without PLX4032 treatment and the effect on apoptotic hallmark proteins expression. (A) PDV cells were treated with mint essential oils or compounds in the presence or absence of 0.5 μM PLX4032. After 24 h, cells were co-stained with Annexin V and propidium iodide and fluorescent expression was detected by flow cytometry. Percentage of apoptotic cells included Annexin V positive/PI negative and Annexin V positive/PI positive. Vehicle controls were obtained from cells treated with 0.5% DMSO. (B) PDV cells were administrated with or without 0.5 μM PLX4032 and/or indicated concentrations of mint essential oils or compounds. After 6 h, cell lysates were collected and PARP and caspase 3 proteins were detected. Vehicle controls were obtained from cells treated with 0.5% DMSO. The data are representative of three independent experiments and are expressed as mean±SD. V: vehicle, P: PLX4032 0.5 μM, KWM: Kenting Water Mint 75 μg/mL, LM: Lime Mint 75 μg/mL, L+C: Limonene+Carvone 60 μg/mL.

Example 5 Mint Essential Oils Induce Apoptosis in PDV Cells with or without PLX4032 Co-Treatment As sub-$G_1$ DNA was observed to be significantly increased in the PDV cells treated with EOs, the percentage of apoptotic cells was further quantified using Annexin V and propidium iodide double staining and analyzed by flow cytometry. Annexin V, a phospholipid-binding protein, has a great affinity for phosphatidylserine that translocates from the inner plasma membrane to the outer leaflet when cells are actively undergoing apoptosis (B. Schutte, R. Nuydens, H. Geerts, et al., *Annexin V binding assay as a tool to measure apoptosis in differentiated neuronal cells. Journal of Neuroscience Methods*, 1998. 86(1): p. 63-69). Propidium iodide is used to discriminate living cells from dead populations. The result in FIG. 6A shows that treatment with 75 μg/mL KWM-EO or 75 μg/mL LM-EO, with or without PLX4032 co-treatment significantly induced the apoptotic cell population 86.9% and 84.5% relative to vehicle-treated cells. PLX4032 (0.5 μM) treatment did not cause apoptosis. The combinational treatment of L+C 40-60 μg/mL did not cause apoptosis in PDV cells with or without PLX4032 co-treatment.

Figure 6B:
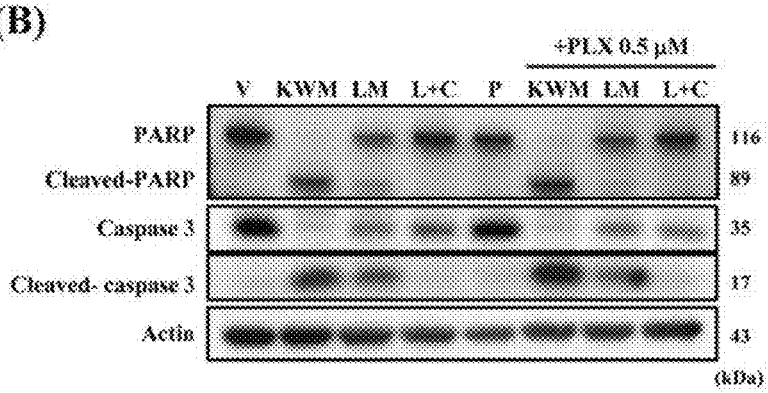

Apoptotic cell death is induced by activating of a group of cysteine proteases caspases. In the process of apoptosis, the apoptosome cleaves the pro-caspase form into its active form of caspase 9, which activates the effector, caspase 3 afterward. Poly (ADP-ribose) polymerase (PARP) is then activated to repair the damaged DNA. The expression levels of caspase 3 and PARP were detected by western blotting (FIG. 6B). The original form of caspase 3 was cleaved to its active form after 75 μg/mL KWM-EO and LM-EO treatment for 6 h. While, active cleavage form of PARP was observed after cells were treated with both EOs for 6 h. The most significant effect was observed in KWM-EO treatment. However, L+C treatment did not affect those apoptotic marker proteins.

Example 6 PLX4032 Induced Paradoxical MAPK Activation in PDV Cells

Figure 7:
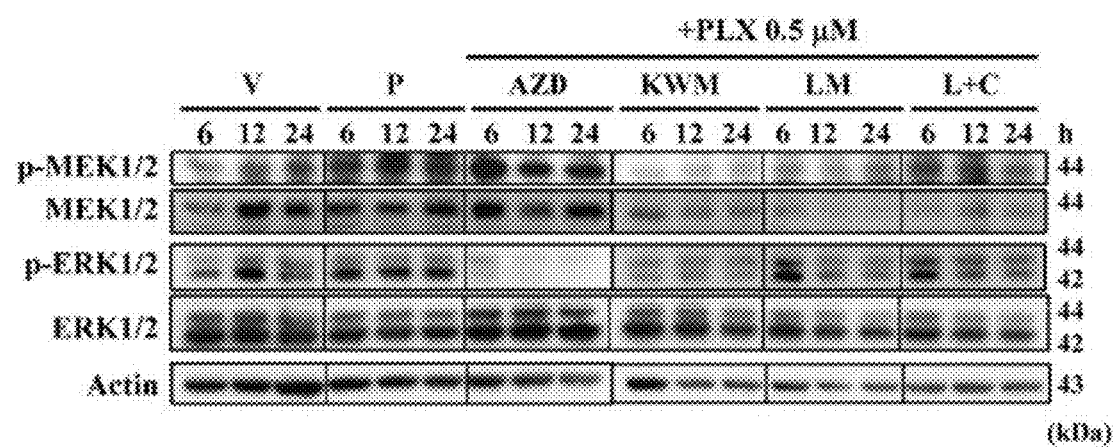
FIG. 7 shows the effect of mint essential oils on paradoxical MAPK activation related proteins expression. PDV cells were co-treated with 0.5 μM PLX4032 and 75 μg/mL mint essential oils or 60 μg/mL compounds for 6, 12, 24 h and detected the expression of MAPK signaling related proteins. Vehicle controls were obtained from cells treated with 0.5% DMSO. V: vehicle, AZD: AZD6244 (MEK inhibitor) 0.5 μM, P: PLX4032 0.5 μM, KWM: Kenting Water Mint 75 μg/mL, LM: Lime Mint 75 μg/mL, L+C: Limonene+Carvone 60 μg/mL FIGS. 8(A) and (B) show the effect of mint essential oils on NO inhibition of LPS-stimulated RAW264.7 macrophages. (A) M. aquatica var. Kenting Water Mint (B) M. aquatica var. citrata Lime Mint. Cells were pre-treated with essential oils at concentrations ranging from 0 to 100 μg/mL for 1 h and then incubated with or without 0.1 μg/mL LPS for 24 h. Vehicle controls were obtained from cells treated with 0.5% DMSO. The data are representative of three independent experiments and are expressed as mean±SD.

It is well known that BRAF inhibitor PLX4032 can induce paradoxical MAPK activation and cause abnormal cell proliferation in RAS mutation cells. The expression level of MAPK signaling pathway related proteins in PDV cells was examined by western blotting (FIG. 7). PLX4032 at 0.5 μM promoted p-MEK and p-ERK protein expression at 6-24 h treatment. MEK inhibitor, AZD6244 reversed the up-regulation of p-ERK induced by PLX4032, while KWM-EO, LM-EO at 75 μg/mL and L+C at 60 μg/mL significantly abolished the p-MEK and p-ERK protein expression in PLX4032-stimulated PDV cells. KWM-EO, LM-EO and L+C treatment also decreased the expression of MEK but not ERK.

Figure 8A:
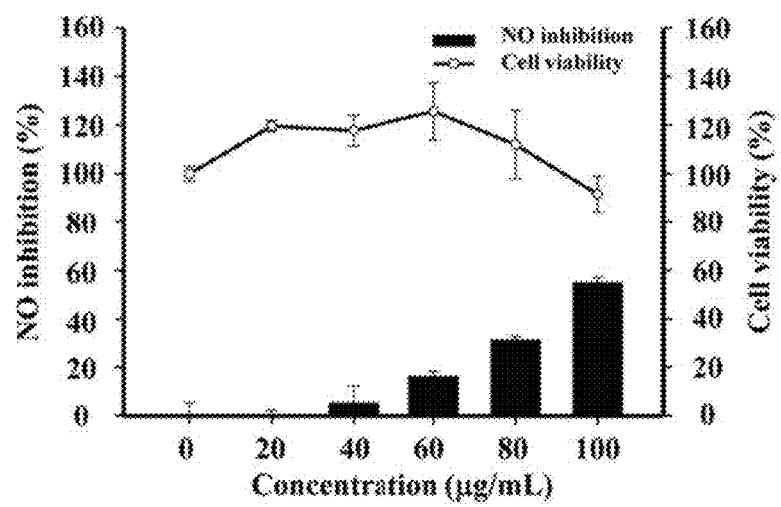
Figure 8B:
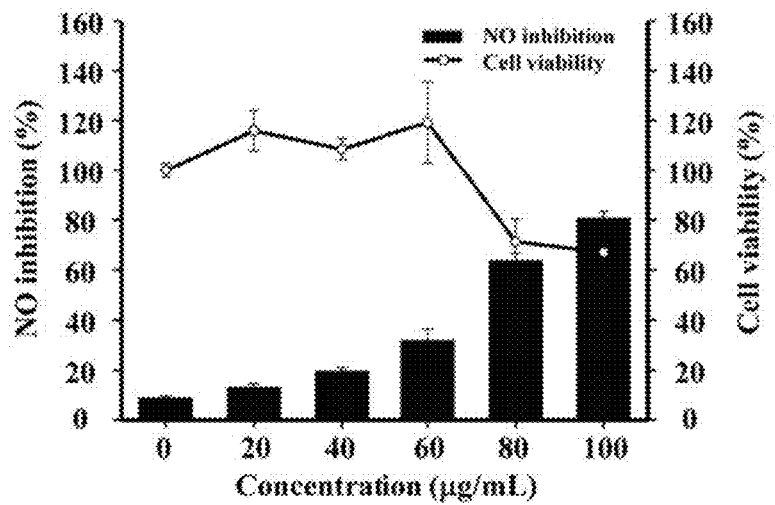

Example 7 Mint Essential Oils Attenuate LPS-Stimulated Nitric Oxide Production in RAW264.7 Macrophages The potential anti-inflammatory activity of mint essential oils (EOs) was assessed by nitric oxide (NO) production on LPS-stimulated murine RAW264.7 macrophages. The cell viability of macrophages with EO treatment was examined in parallel. LM-EO and KWM-EO show inhibitory activity on NO production in the LPS-stimulated RAW264.7 cells with $IC_{50}$ values of 86.5 and 95.8 μg/mL, respectively (FIG. 8). Meanwhile, both mint essential oils have little or no detectable cytotoxicity to RAW264.7 cells at the same measured concentrations up to 100 μg/mL.

Figure 9A:
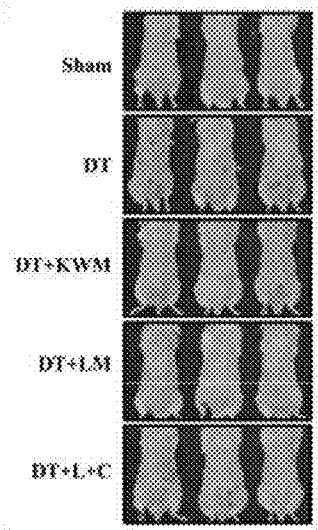
FIGS. 9(A) to (F) show the effect of mint essential oils on papilloma induction in response to DMBA/TPA treatment. (A) Representative images show the results at week 12. (B) The tumor incidence was calculated every week over 12 weeks of treatment. (C) The mean number of papillomas per mouse were recorded over 12 weeks of treatment. (D) The dot plot shows tumors amount per mouse at week 12. Median of papillomas number per group are presented. (E) Mouse body weights were measured every week. (F) Organ weights were recorded after mice were sacrificed at week 12. The organ index was calculated by the following formula: organ index=organ weight/body weight. Each group consisted of 8 mice. The data are presented as the mean±SD. D: DMBA, T: TPA, KWM: Kenting Water Mint, LM: Lime Mint, L+C: Limonene+Carvone.
Figure 9B:
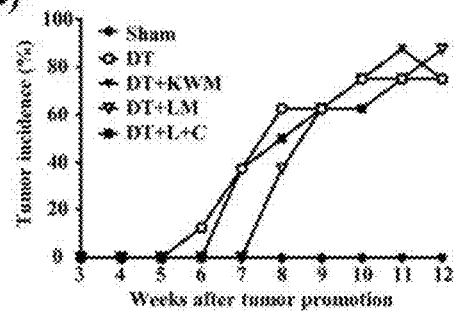
Figure 9C:
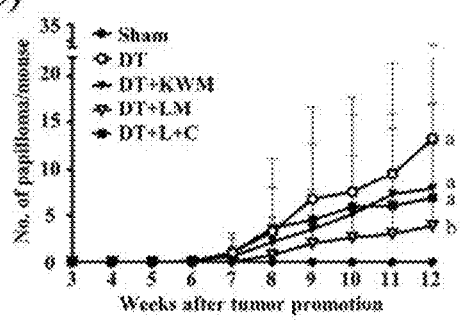
Figure 9D:
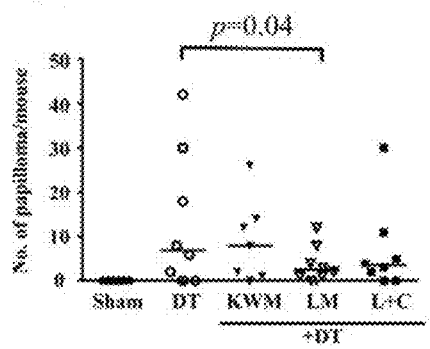
Figure 9E:
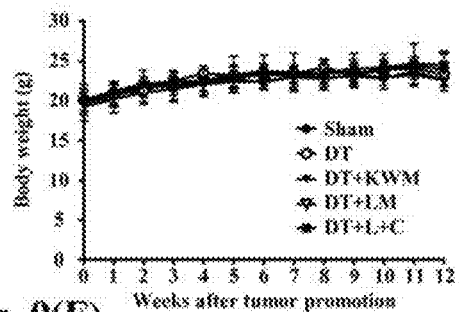
Figure 9F:
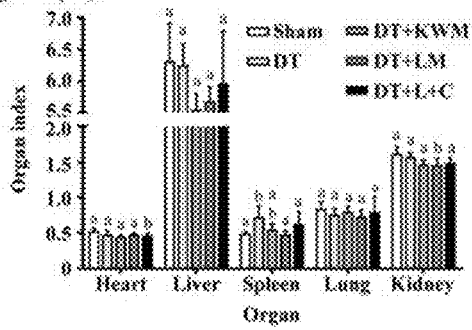

Example 8 Mint Essential Oils Attenuated DMBA/TPA-Induced Skin Carcinogenesis The chemopreventive effect of mint essential oils was investigated using a two-stage skin carcinogenesis mouse model. FIG. 9A shows that by initiator DMBA and promoter TPA irritation (DMBA/TPA) mouse dorsal skin formed papillomas successfully. The multiplicity stimulated by DMBA/TPA treatment was suppressed by KWM-EO, LM-EO and L+C topical treatments. Of note, LM-EO displayed the best effect (FIG. 9B). Compared to the DMBA/TPA group, LM-EO and L+C delayed the appearance of lesions from 5 to 7 weeks and 5 to 6 weeks, respectively. After treatment for 12-weeks, the papilloma incidence of the DMBA/TPA group, KWM-EO and L+C group reached 75% (FIG. 9C). Although the incidence of LM-EO treated group reached 87.5%, higher than the DMBA/TPA group, the mean number of papillomas was significantly reduced in the LM-EO treated group mice, as shown in FIG. 9D. The median of LM-EO and the L+C compound treatment group were smaller compared to the DMBA/TPA group (FIG. 9D). Mouse body weights were recorded weekly, and the data showed that there was no difference within the groups (FIG. 9E). Organ index enables a comparison of the extent of damage caused by a toxicant in different organs. At the end of the experiment (12 weeks), internal organs were collected and the ratio of organ weight versus body weight was calculated to gain the specific organ index. It is known that in the two-stage skin carcinogenesis model, the mouse spleen weight is increased. The swelling of the spleen was reversed by KWM-EO, LM-EO and L+C treatment (FIG. 9F).

Example 9 Mint Essential Oils Attenuated DMBA/TPA-Induced Skin Carcinogenesis Accelerated by PLX4032

Figure 10A:
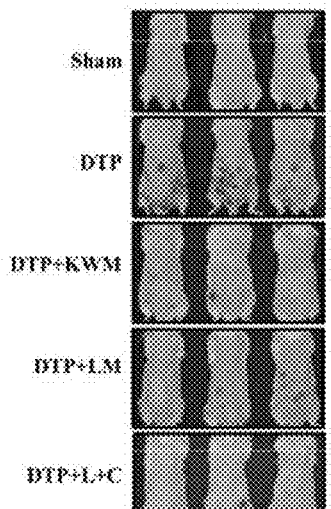
FIGS. 10(A) to (F) show effect of mint essential oils on papilloma induction in response to DMBA/TPA/PLX4032 treatment. (A) Representative images show the results at week 12. (B) The tumor incidence was calculated every week over 12 weeks of treatment. (C) The mean number of papillomas per mouse were recorded over 12 weeks of treatment. (D) Dot plot shows tumors amount per mouse at week 12. Median of papillomas number per group are presented. (E) Mouse body weights were measured every week. (F) Organ weights were recorded after mice were sacrificed at week 12. Organ index was calculated by the following formula: organ index=organ weight/body weight. Each group consisted of 8 mice. The data are presented as the mean±SD. D: DMBA, T: TPA, P: PLX4032, KWM: Kenting Water Mint, LM: Lime Mint, L+C: Limonene+Carvone.
Figure 10B:
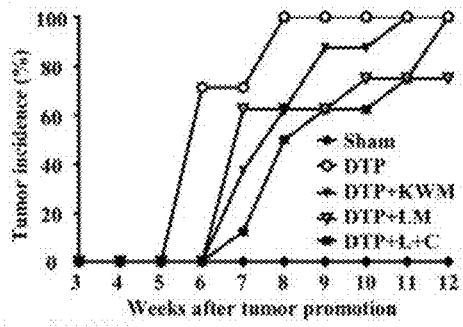
Figure 10C:
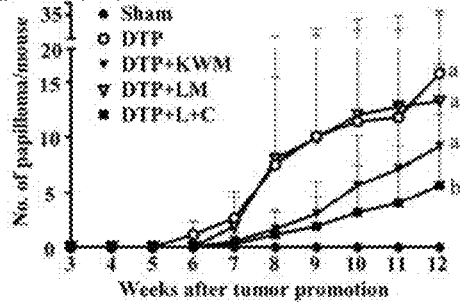
Figure 10D:
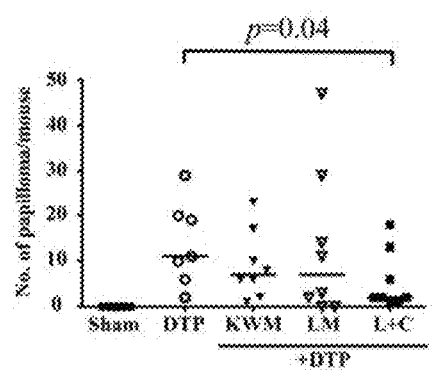
Figure 10E:
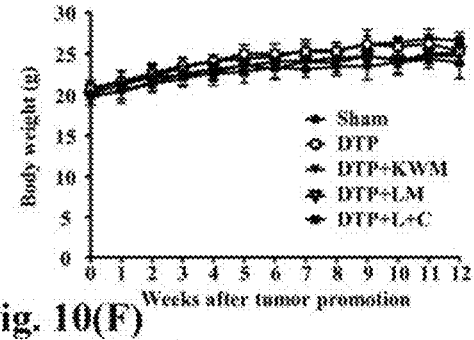
Figure 10F:
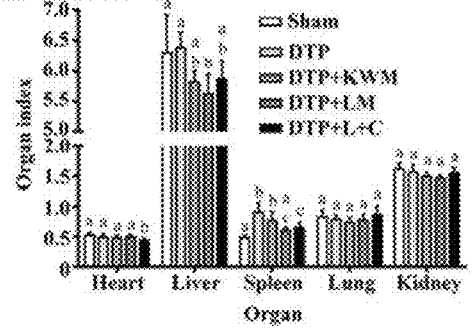

The chemopreventive effect of mint essential oils on DMBA/TPA-induced skin epithelia papilloma accelerated by BRAF inhibitor was further investigated. FIG. 10A shows that DMBA/TPA treated dorsal papillomas were notably facilitated by PLX4032 treatment. As described previously, PLX4032 greatly increased the tumor multiplicity. Topical application of L+C combination significantly reduced the average number of skin papilloma per mouse, KWM-EO and LM-EO treatment slightly decreased the average number of papillomas (FIG. 10B). In addition, intraperitoneal injection of PLX4032 accelerated the appearance of palpable DMBA/TPA induced skin papillomas, and all mice were burdened with papillomas after repeated application of TPA and PLX4032 for 8-weeks. KWM-EO, LM-EO and L+C treatment delayed the emergence of papilloma. All of them showed delayed latency period from 5 to 6 weeks. After the 12-week experiment, the papilloma incidence in the DMBA/TPA/PLX4032 group, KWM-EO and L+C treated groups reached 100%; however, the incidence was decreased by LM-EO application at 75% (FIG. 10C). The median of the L+C treated group was smaller than the DMBA/TPA/PLX4032 group (FIG. 10D). Mouse body weights were measured weekly, with no effect on mouse weight being observed (FIG. 10E). After observation for 12 weeks, the internal organs were collected and the ratio of organ weight versus body weight was calculated to gain the specific organ index. Treatment with PLX4032 exacerbated the swelling of the spleen, which was in turn reverted by KWM-EO, LM-EO and L+C compounds treatment (FIG. 10F).

Example 10 Immunopathology of Mouse Skin

Figure 11:
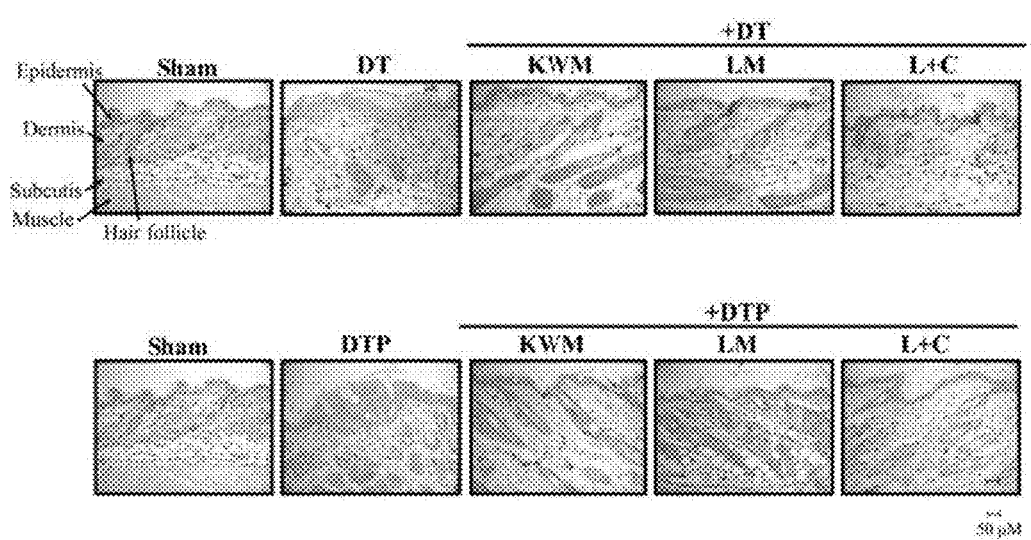
FIG. 11 shows histological examination of skin sections from a two-stage skin carcinogenesis model. Dorsal skins of female FVB mice topically treated with DMBA/TPA or DMBA/TPA/PLX4032 and the indicated concentrations of mint essential oils or compounds. The morphology of the tissue was detected by double staining of hematoxyline and eosin. Representative images from among eight treated mice in each group are shown. Images were taken by using Carl Zeiss Axio Imager. Z1 microscopes (magnification: ×200). D: DMBA, T: TPA, P: PLX4032, KWM: Kenting Water Mint, LM: Lime Mint, L+C: Limonene+Carvone.

H&E staining was performed to examine the histopathology of mouse skin tissues (FIG. 11). The typical skin architecture with epidermis, dermis, subcutis, muscle and hair follicles were observed in sham group mice. Topical application of DMBA/TPA resulted in an increase in epidermal thickness which is suggested to be abnormal proliferation and hyperplasia of the epidermis. The irregular thickness of the epidermis was attenuated by KWM-EO, LM-EO and L+C combination treatment. In DMBA-initiated and TPA-promoted skin, intraperitoneal injection of PLX4032 exacerbated the proliferation and hyperplasia of the epidermis. Mint EOs and major compound application also notably inhibited the unnatural thickness of the epidermis.

Figure 12:
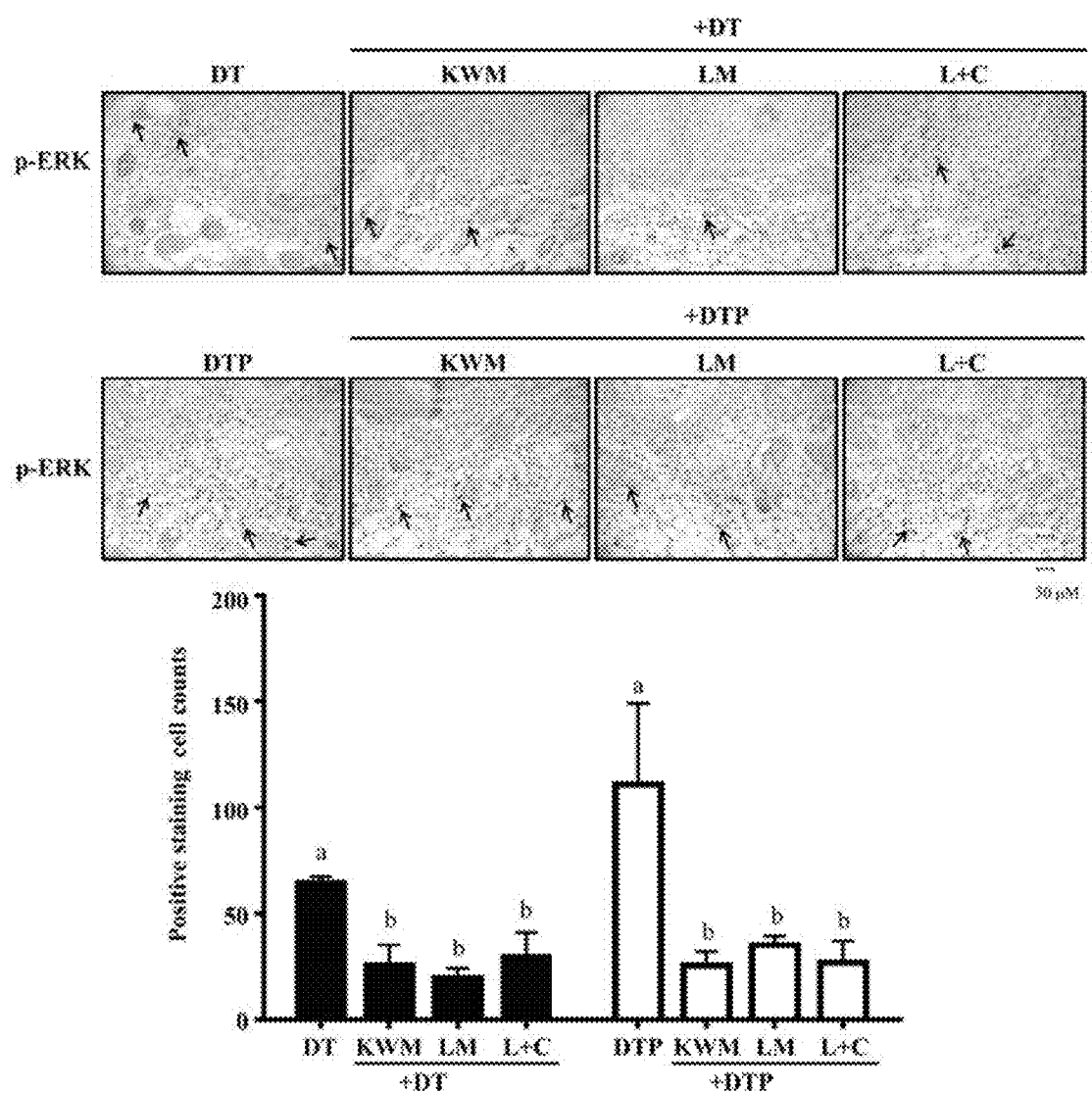
FIG. 12 shows immunohistochemical analysis of the effect of mint essential oils and compounds on MAPK signaling of papillomas from two-stage skin carcinogenesis. Papillomas from DMBA/TPA-stimulated mice with or without PLX4032 acceleration were treated with mint essential oils or compounds and the positive expression of p-ERK was detected after 12 weeks administration. Representative images from among eight treated mice in each group are shown. Images were taken by using Carl Zeiss Axio Imager. Z1 microscopes (magnification: ×200).

Example 11 Paradoxical MAPK Activation was Suppressed by Mint Essential Oils in Papilloma Tissue Phosphorylation of ERK is an important hallmark of the MAPK signaling pathway that regulates cell proliferation, division, motility and death. The protein expression level of p-ERK in papillomas was further analyzed by IHC. Most of the p-ERK protein were expressed between the junction of subcutaneous layer and papillomas in DMBA/TPA-irritated mice skin and that can be down-regulated by KWM-EO, LM-EO and L+C treatments (FIG. 12). Previous study indicated that PLX4032 injection enhanced the activation of p-ERK on RAS gene mutated tissue that is also observed nicely in this study. The paradoxical activation of p-ERK was significantly blockaded by KWM-EO, LM-EO and L+C topical applications.

Example 12 The Anti-Cancer Cell Effect of EOs

Figure 13A:
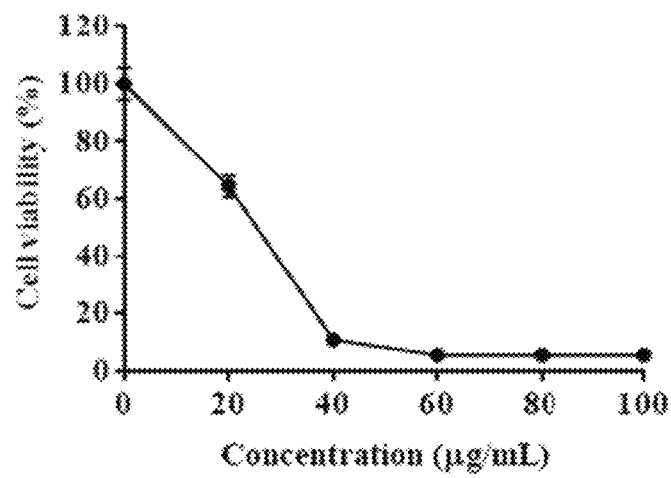
FIGS. 13(A) and (B) show the anti-cancer cell activity of two mint essential oils on B16 melanoma cells. B16 cells were treated with indicated concentrations of LM-EO (A) or KWM-EO (B) for 24 h, and the cell viability was determined by MTT assay.
Figure 13B:
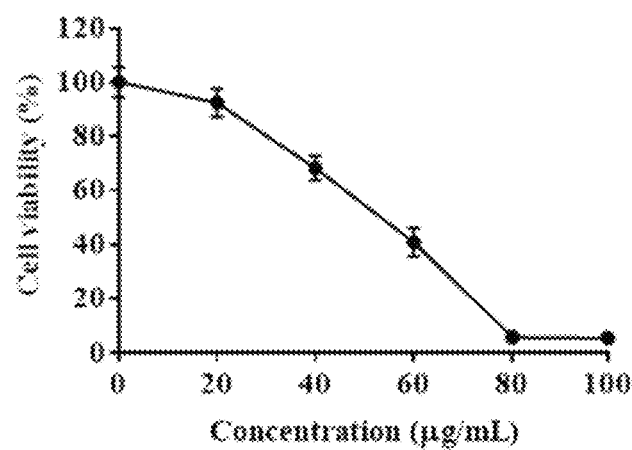

The anti-cancer cell proliferation effect of LM-EO and KWM-EO against B16 melanoma cells was determined by MTT assay. The results in FIG. 13 reveal that both LM-EO and KWM-EO inhibited B16 melanoma cells viability dose-dependently. The $IC_{50}$ of LM-EO on B16 cells was 25.39 µg/mL (FIG. 13A) and KWM-EO was 53.32 µg/mL (FIG. 13B).

Example 13 The Depigmentation Activity of LM-EO

Figure 14A:
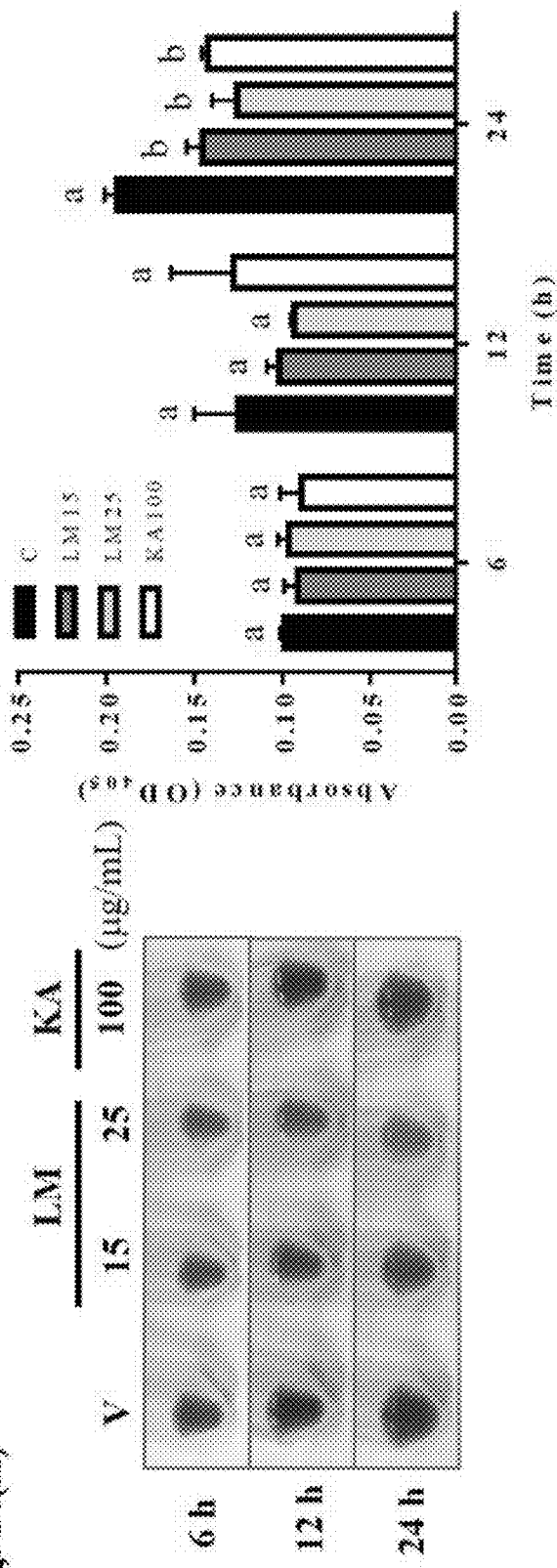
FIGS. 14(A) and (B) show the depigmentation effect of LM-EO and kojic acid on B16 melanoma cells. B16 cells were treated with vehicle (0.5% DMSO), 15 and 25 μg/mL LM-EO, and 100 μg/mL KA for 6, 12, 24 h. The photos of treated cells (A) and absorbance of melanin dissolved in NaOH was measured at 405 nm. (B). The total cellular proteins of B16 cells with the same treatment were subjected to western blotting. The expression level of tyrosinase was detected. Actin was used as internal control.
Figure 14B:
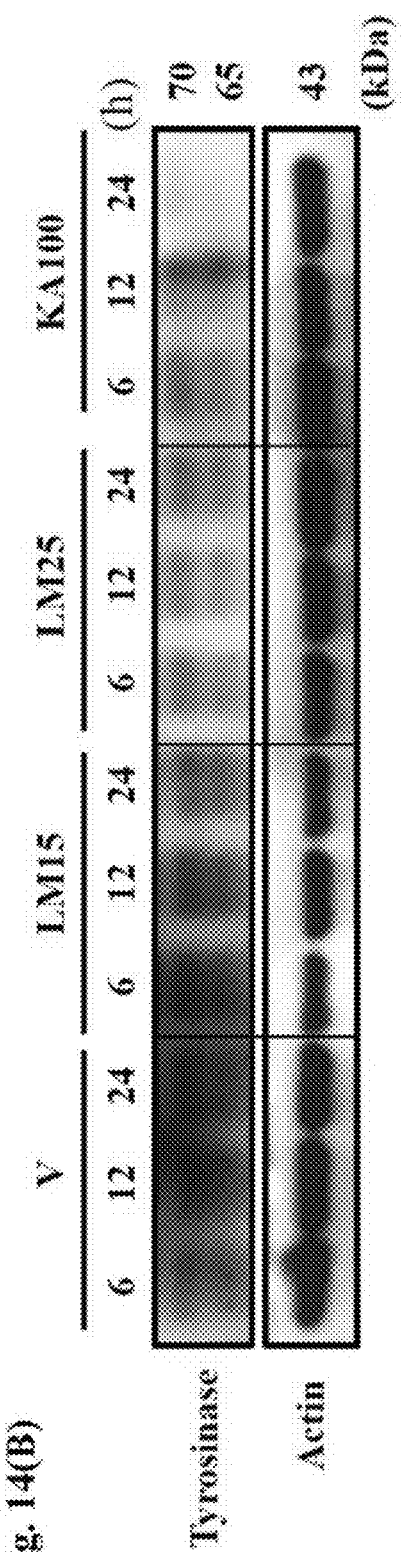

The depigmentation or anti-melanogenesis activity of LM-EO was examined. Kojic acid (KA), commonly used in skin-lightening cosmetic products in cosmetic industries was selected as the positive control. The photo images of the B16 cells treated with LM-EO or KA for 6, 12 and 24 h showed that LM-EO might have depigmentation effect (FIG. 14A). Further quantification data shown in FIG. 14A indeed revealed that when the cells were treated for 24 h, 15 and 25 µg/mL LM-EO, and 100 µg/mL KA all showed depigmentation effect with statistical significance. Tyrosinase is a key protein in the process of melanin formation, the expression level of tyrosinase was investigated by western blotting. The data in FIG. 14B show that either LM-EO or KA time-dependently inhibited tyrosinase expression in B16 cells that can be referred to their depigmentation effect. The results indicate that the essential oils from *M. aquatica* var. Citrata Lime Mint can be further development into skin-whitening or pigmentation reduction products.

Example 14 Further Isolation of Essential Oil Components

The isolated components can be obtained as boiling point fractionations using the steam-based distillation methods and liquid-liquid extraction methods described herein to further isolate the essential components. The boiling points of each of the essential oil components of Table 1 are known in the art, and may be used to further isolate the component from an essential oil mixture using careful vapor-distillation methods with condenser tubes with a large number of theoretical plates. Isolated components can exhibit markedly different properties from the cumulative mixture in the essential oil by the absence of properties imparted by the removed components (e.g., viscosity, tackiness, odor, total vapor pressure, skin penetrance, etc.). In some embodiments, a change in a smell profile may be desired to reduce unpleasant odor in the pharmaceutical compositions comprising the isolated essential oil components. Isolating and optionally re-combining selected components of the essential oil composition less the component imparting the unpleasant odor can be performed using the methods described herein. In some embodiment, a skin penetrant may be desired to be removed for treatment of skin conditions where the skin comprises an open wound so as to reduce pain during administration. Isolating and optionally re-combining selected components of the essential oil composition less the component imparting the skin penetrance (e.g., Levomenthol) can reduce paid during topical administration of the recombined essential oil components.

In some embodiments, it may be desired to remove toxic components of the essential oil composition (e.g., Menthofuran). The isolated essential oil components can be isolated using the methods described herein to remove said toxic components, and re-combine the remainder components to form an essential oil composition which is markedly different from the natural composition in that the toxic components have been removed.

We claim:

1. A method for inhibiting $HRAS^{Q61L}$ mutant keratinocyte activity in a subject in need thereof or treating skin carcinogenesis associated with $HRAS^{Q61L}$ mutant keratinocyte activity in a subject in need thereof, comprising topically applying to skin of said subject an essential oil composition comprising a therapeutically effective amount of the extracted essential oil composition of an *M. aquatica* varietal selected from *M. aquatica* var. Kenting Water Mint or *M. aquatica* var. citrata Lime Mint,
wherein the therapeutically effective amount of the essential oil composition is topically applied in an amount ranging from about 0.1 mg to about 10 mg/site.

2. The method of claim 1, wherein the essential oil composition comprises an essential oil from *M. aquatica* var. Kenting Water Mint and an essential oil from *M. aquatica* var. citrata Lime Mint.

3. The method of claim 1, wherein the skin carcinogenesis is the development of squamous cell carcinoma (SCC).

4. The method of claim 1, wherein the essential oil composition inhibits inflammation.

5. The method of claim 1, wherein the essential oil composition prevents a two-stage skin carcinogenesis.

6. The method of claim 5, wherein the skin carcinogenesis is a chemical or drug-induced two-stage skin carcinogenesis.

7. The method of claim 6, wherein the drug is BRAF-inhibitor.

8. The method of claim 1, wherein the essential oil composition exhibits anti-proliferation effects against $HRAS^{Q61L}$ keratinocytes.

9. The method of claim 1, wherein the essential oil composition induces $G_2$/M cell-cycle arrest and cell apoptosis.

10. The method of claim 1, wherein the essential oil composition inhibits papilloma formation.

11. The method of claim 1, wherein the essential oil composition diminishes reactivation of MAPK signaling.

12. A method for inhibiting $HRAS^{Q61L}$ mutant keratinocyte activity in a subject in need thereof or treating skin carcinogenesis associated with $HRAS^{Q61L}$ mutant keratinocyte activity in a subject in need thereof, comprising topically applying to the skin of said subject a composition comprising a therapeutically effective amount of α-pinene or β-pinene.

13. The method of claim 1, wherein the essential oil composition comprises at least one of α-pinene and β-pinene.

\* \* \* \* \*